United States Patent
Adler

(10) Patent No.: US 10,932,863 B2
(45) Date of Patent: *Mar. 2, 2021

(54) METHODS OF CARDIAC MAPPING AND DIRECTIONAL GUIDANCE

(71) Applicant: CATHETER PRECISION, INC., Ledgewood, NJ (US)

(72) Inventor: Steve Adler, Randolph, NJ (US)

(73) Assignee: Catheter Precision, Inc., Ledgewood, NJ (US)

(*) Notice: Subject to any disclaimer, the term of this patent is extended or adjusted under 35 U.S.C. 154(b) by 259 days.

This patent is subject to a terminal disclaimer.

(21) Appl. No.: 16/050,532

(22) Filed: Jul. 31, 2018

(65) Prior Publication Data

US 2019/0038363 A1  Feb. 7, 2019

Related U.S. Application Data

(60) Provisional application No. 62/539,740, filed on Aug. 1, 2017, provisional application No. 62/711,777, filed on Jul. 30, 2018.

(51) Int. Cl.
*A61B 18/14* (2006.01)
*A61B 5/044* (2006.01)
(Continued)

(52) U.S. Cl.
CPC ............ *A61B 34/20* (2016.02); *A61B 5/0044* (2013.01); *A61B 5/044* (2013.01);
(Continued)

(58) Field of Classification Search
CPC .......... A61B 5/044; A61B 2018/00351; A61B 2018/00839
See application file for complete search history.

(56) References Cited

U.S. PATENT DOCUMENTS 5,657,755 A * 8/1997 Desai ................... A61B 5/0422
600/374
7,787,951 B1 8/2010 Min
(Continued)

FOREIGN PATENT DOCUMENTS

| WO | 2012061612 A2 | 5/2012 |
| WO | 2013006713 A2 | 1/2013 |
| WO | 2015170978 A1 | 11/2015 |

OTHER PUBLICATIONS

Daubert, et al., "Avoiding non-responders to cardiac resynchronization therapy: a practical guide", European Heart Journal Advance Access, European Heart Journal, doi:10.1093/eurheartj/ehw270, 13 pages, (Jul. 1, 2016).

(Continued)

*Primary Examiner* — George R Evanisko
(74) *Attorney, Agent, or Firm* — The Marbury Law Group, PLLC

(57) ABSTRACT

Various embodiments provide a cardiac mapping method including: generating an activation map of a heart based on electrocardiogram (ECG) data of a heart and a three-dimensional (3D) heart model; performing an electrophysiology (EP) procedure to determine a first pacing location; pacing the heart at the first pacing location using an EP catheter; determining whether the pacing at the first pacing location generates a desired cardiac response; displaying guidance information related to a second pacing location on one or both of the activation map and the internal surface map, when the first pacing location is determined not to generate the desired cardiac response; moving the pacing catheter to the second pacing location, based on the guidance information; and pacing the heart at the second pacing location.

22 Claims, 21 Drawing Sheets

(51) Int. Cl.
- *A61B 34/20* (2016.01)
- *A61N 1/368* (2006.01)
- *A61B 34/10* (2016.01)
- *A61B 34/00* (2016.01)
- *A61B 5/00* (2006.01)
- *A61N 1/372* (2006.01)
- *A61B 18/00* (2006.01)
- *A61N 1/365* (2006.01)
- *A61B 5/0402* (2006.01)
- *A61B 90/00* (2016.01)

(52) U.S. Cl.
CPC .......... *A61B 18/1492* (2013.01); *A61B 34/10* (2016.02); *A61B 34/25* (2016.02); *A61N 1/3686* (2013.01); *A61N 1/372* (2013.01); *A61B 5/0402* (2013.01); *A61B 2018/00351* (2013.01); *A61B 2018/00577* (2013.01); *A61B 2018/00642* (2013.01); *A61B 2018/00839* (2013.01); *A61B 2034/105* (2016.02); *A61B 2034/2051* (2016.02); *A61B 2034/2057* (2016.02); *A61B 2034/2072* (2016.02); *A61B 2090/363* (2016.02); *A61B 2090/364* (2016.02); *A61B 2090/367* (2016.02); *A61N 1/36507* (2013.01); *A61N 1/37247* (2013.01)

(56) References Cited

U.S. PATENT DOCUMENTS

| | | | |
|---|---|---|---|
| 8,155,739 | B2 | 4/2012 | Keel et al. |
| 2009/0099679 | A1 | 4/2009 | Sandoval et al. |
| 2010/0268059 | A1 | 10/2010 | Ryu et al. |
| 2012/0157822 | A1 | 6/2012 | Van Dam et al. |
| 2017/0011197 | A1 | 1/2017 | Van Dam et al. |

OTHER PUBLICATIONS

Ploux, et al., "Noninvasive Electrocardiographic Mapping to Improve Patient Selection for Cardiac Resynchronization Therapy", Cardiac Resynchronization, Journal of the American College of Cardiology, vol. 61, No. 24, ISSN 00735-1097, 9 pages, (2013).

International Search Report and the Written Opinion of the International Searching Authority from the European Patent Office in Application No. PCT/US2017/050188 dated Nov. 7, 2017.

* cited by examiner

METHODS OF CARDIAC MAPPING AND DIRECTIONAL GUIDANCE

CROSS-REFERENCE TO RELATED APPLICATION

This application claims the benefit of priority to U.S. Provisional Patent Application No. 62/539,740, entitled "METHODS OF CARDIAC MAPPING AND DIRECTIONAL GUIDANCE", filed Aug. 1, 2017, and U.S. Provisional Patent Application No. 62/711,777, entitled "CARDIAC MAPPING SYSTEMS, METHODS, AND KITS INCLUDING FIDUCIAL MARKERS", filed Jul. 30, 2018, the entire contents of both of which are hereby incorporated by reference for all purposes.

BACKGROUND

Some heart defects in the conduction system result in asynchronous contraction (arrhythmia) of the heart and are sometimes referred to as conduction disorders. As a result, the heart does not pump enough blood, which may ultimately lead to heart failure. Conduction disorders can have a variety of causes, including age, heart (muscle) damage, medications and genetics.

Premature Ventricular Contractions (PVCs) are abnormal or aberrant heart beats that start somewhere in the heart ventricles rather than in the upper chambers of the heart as with normal sinus beats. PVCs typically result in a lower cardiac output as the ventricles contract before they have had a chance to completely fill with blood. PVCs may also trigger Ventricular Tachycardia (VT or V-Tach).

Ventricular tachycardia (VT or V-Tach) is another heart arrhythmia disorder caused by abnormal electrical signals in the heart ventricles. In VT, the abnormal electrical signals cause the heart to beat faster than normal, usually more than 100 beats per minute, with the beats starting in the heart ventricles. VT generally occurs in people with underlying heart abnormalities. VT can sometimes occur in structurally normal hearts, and in such patients the origin of abnormal electrical signals can be in multiple locations in the heart. One common location is in the right ventricular outflow tract (RVOT), which is the route the blood flows from the right ventricle to the lungs. In patients who have had a heart attack, scarring from the heart attack can create a milieu of intact heart muscle and a scar that predisposes patients to VT.

Other common causes for conduction disorders include defects in the left and/or right ventricle fast activation fibers, the His-Purkinje system, or scar tissue. As a result, the left and right ventricles may not be synchronized. This is referred to as Left Bundle Branch Block (LBBB) or Right Bundle Branch Block (RBBB).

Cardiac resynchronization therapy (CRT), also referred to as biventricular pacing or multisite ventricular pacing, is a known way to improve heart function in cases of LBBB or RBBB. CRT involves simultaneous pacing of the right ventricle (RV) and the left ventricle (LV) using a pacemaker. To implement CRT, a coronary sinus (CS) lead is placed for LV pacing in addition to a conventional RV endocardial lead (with or without a right atrial (RA) lead). The basic goal of CRT is to improve the mechanical functioning of the LV by restoring LV synchrony in patients with dilated cardiomyopathy and a widened QRS period, which is predominantly a result of LBBB.

Catheter ablation is a treatment of choice in patients with VT and/or symptomatic PVCs. The targets for ablation are locations in the heart where PVCs are occurring or locations where the onset of the VT is occurring. In order to determine a proper ablation location, a treating physician may first stimulate a proposed location using an electrical lead, in order to determine whether ablation at the proposed location will provide a desired electrical activation pattern stimulation of the heart.

Currently, determining the proper positioning of leads to obtain maximum cardiac synchronization or a desired electrical activation pattern involves a certain amount of guesswork on the part of an operating physician.

However, current methods do not allow for the determination of the optimal location for electrical leads, on a patient by patient basis. Further, if a desired activation pattern is not achieved when the heart is stimulated at a given location, current methods do not provide directional guidance for adjusting the lead location to provide an improved activation pattern. Accordingly, there is a need for improved guidance in determining the proper location for electrical leads for CRT and determining ablation locations.

SUMMARY

Various embodiments provide improved cardiac imaging methods for determining locations for placing pacing electrodes within the heart.

Some embodiments provide cardiac imaging methods including generating an activation map of a heart based on electrocardiogram (ECG) data of the heart and a three-dimensional (3D) heart model, performing an electrophysiology (EP) procedure to determine a first pacing location, pacing the heart at the first pacing location using a pacing catheter, determining whether the pacing at the first pacing location generates a desired cardiac response, and displaying guidance information related to a second pacing location on one or both of the activation map and the internal surface map when the first pacing location is determined not to generate the desired cardiac response. Such embodiment methods may further include moving the pacing catheter to the second pacing location, based on the guidance information, and pacing the heart at the second pacing location.

Some embodiments provide cardiac imaging methods including generating a PVC activation map of the heart, based on premature ventricular contraction (PVC) electrocardiogram (ECG) data recording during PVC of the heart and a 3D heart model generated based on two-dimensional (2D) images of the hear, pacing the heart at a first pacing location disposed in the area of earliest activation included in the PVC activation map using a catheter, determining whether the first pacing location is an ablation location based on a comparison of the PVC ECG data and ECG data recorded during the pacing of the first pacing location, and displaying guidance information related to a second pacing location if the first pacing location is determined not to be an ablation location. Such embodiment methods may further include moving the catheter to the second pacing location based on the guidance information, and pacing the heart at the second pacing location using the catheter.

Some embodiments provide cardiac imaging methods including generating an activation map of a heart based on electrocardiogram (ECG) data of the heart and a 3D heart model, performing an electrophysiology (EP) procedure to determine a first pacing location; pacing the heart at the first pacing location using a EP catheter, determining whether the pacing at the first pacing location generates at least a set amount of cardiac synchronization, and displaying the guidance information related to a second pacing location on one or both of the activation map and the internal surface map when the first pacing location is determined to generate less than the set amount of synchronization. Such embodiment methods may further include moving the pacing catheter to the second pacing location based on the guidance information, and pacing the heart at the second pacing location.

BRIEF DESCRIPTION OF THE DRAWINGS

The accompanying drawings, which are incorporated herein and constitute part of this specification, illustrate example embodiments of the invention, and together with the general description given above and the detailed description given below, serve to explain the features of the invention.

DETAILED DESCRIPTION

Figure 1:
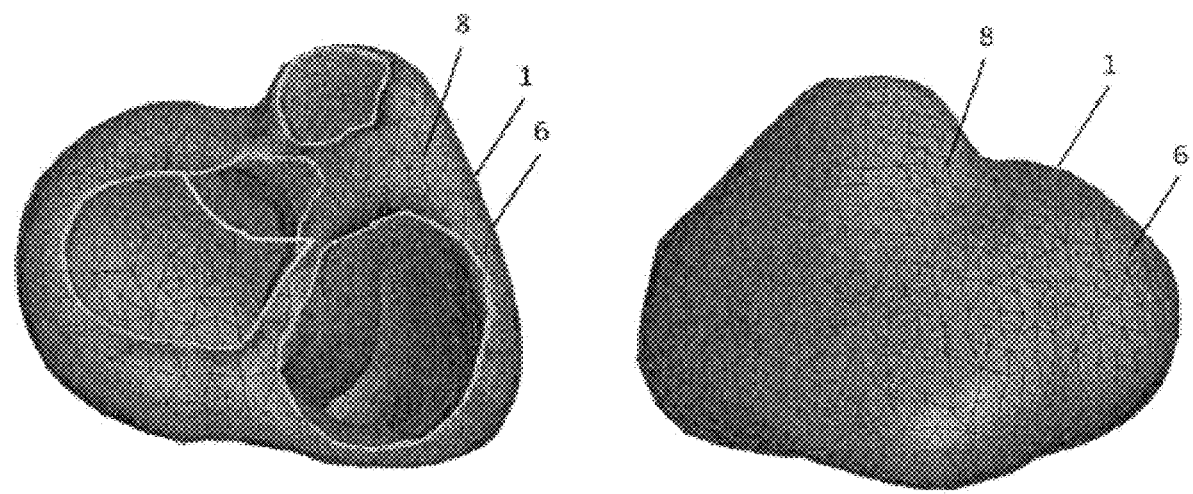
FIG. 1 is an example of a 3D model of a heart according to various embodiments.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

An electrocardiogram (ECG) is defined herein as any method that (preferably non-invasively) correlates actual electrical activity of the heart muscle to measured or derived (electrical activity) of the heart. In case of a classical electrocardiogram the differences in potential between electrodes on the body surface are correlated to the electrical activity of the heart. Derived ECG's can also be obtained in other ways (e.g. by measurement made by a so-called ICD (Implantable Cardioverter Defibrillator)). In order to obtain such a functional image an estimation of the movement of the electrical activity has to be provided.

Cardiac dyssynchrony has deleterious effects on cardiac function by depressing left ventricular (LV) mechanical performance, while increasing myocardial oxygen consumption. In addition, it probably causes LV remodeling. Therefore, cardiac dyssynchrony accelerates the progression of chronic congestive heart failure (CHF) and reduces patient survival.

During normal conduction, cardiac activation begins within both the left ventricular (LV) and right ventricular (RV) endocardium. In particular, electrical impulses (i.e., depolarization waves) travel substantially simultaneously through both the left and right ventricles. Bundle branch block (BBB) is a condition in which there is a delay or obstruction along the pathway of the electrical impulses. The delay or blockage may occur on the pathway that sends electrical impulses to the left or the right ventricles.

Left BBB is a condition in which the electrical impulses to the LV are slowed, and is one of the leading causes of cardiac desynchronization. In particular, activation begins only in the RV and proceeds through the septum before reaching the LV endocardium.

A pacemaker is an electronic device, approximately the size of a pocket watch, which senses intrinsic heart rhythms and provides electrical stimulation when indicated. Cardiac pacing can be either temporary or permanent.

Permanent pacing is most commonly accomplished through transvenous placement of leads to the endocardium (i.e., right atrium or ventricle) or epicardium (i.e., the LV surface via the coronary sinus), which are subsequently connected to a pacing generator placed subcutaneously in the infra-clavicular region. However, miniaturized pacemakers have been developed for implantation directly on or in the heart.

Cardiac resynchronization therapy (CRT) is a specialized type of pacemaker therapy that provides biventricular pacing. CRT is carried out with or without the use of an implantable cardioverter-defibrillator (ICD), a device employed for treatment and prophylaxis in patients at risk for ventricular tachycardia (VT) or ventricular fibrillation (VF).

In this application, areas in the heart that are electrically stimulated (e.g., paced) by a pacing electrode, micro catheter, or the like may be interchangeably referred to as a "pacing location" or a "stimulation location".

FIG. 1 shows a three-dimensional (3D) model of a heart 1 seen in two different directions. The 3D model includes a mesh 6 representing an outer surface of the heart, here the myocardial surface. In this example, the model also may include the septal wall. The mesh 6 has a plurality of nodes 8. In this example, the mesh is a triangular mesh in which the surface of the heart is approximated by adjoining triangles.

Figure 2A:
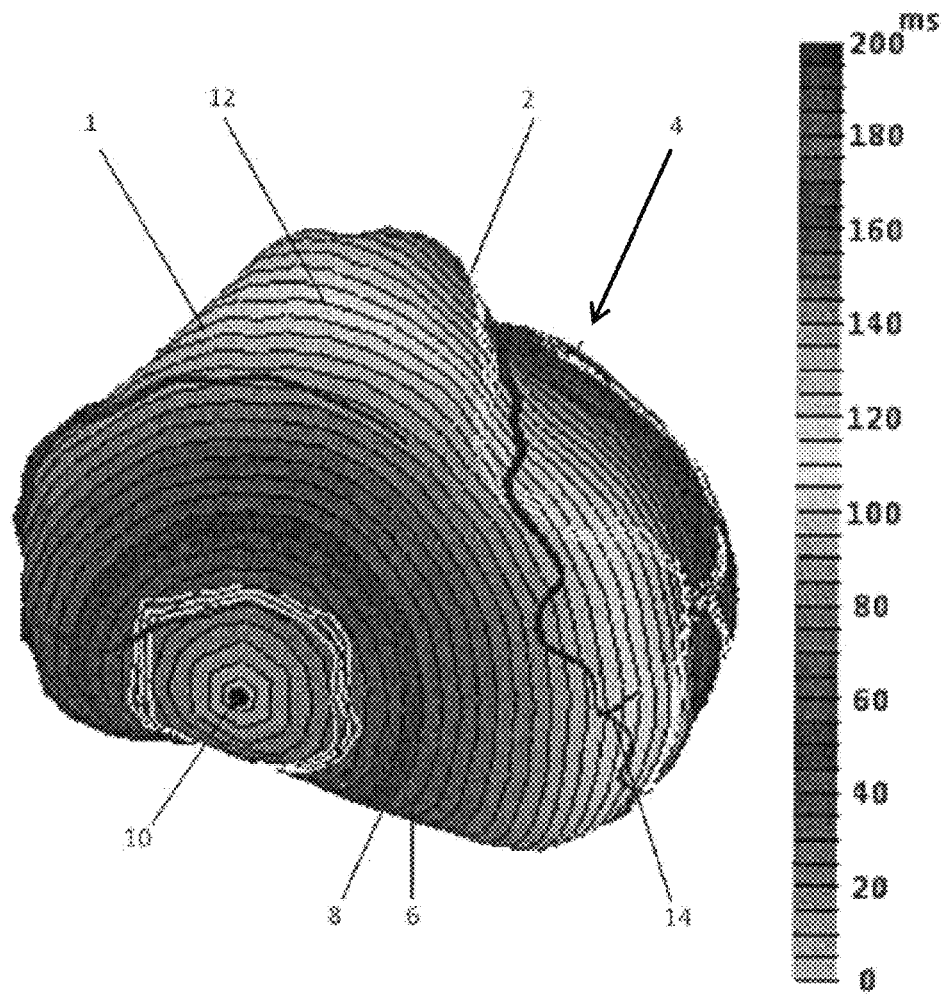
FIG. 2A is a plan view of a 3D model of electrical activation of a heart according to various embodiments.
Figure 2B:
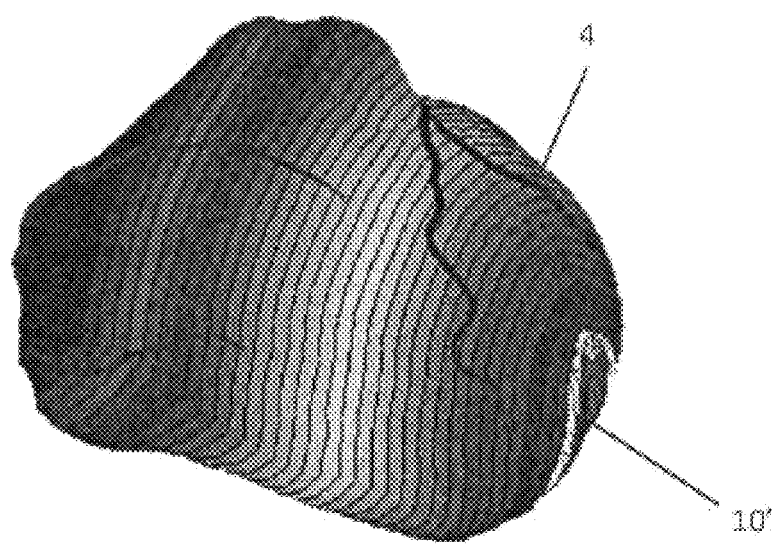
FIG. 2B is a plan view of a 3D model of electrical activation of a heart according to various embodiments.
Figure 2C:
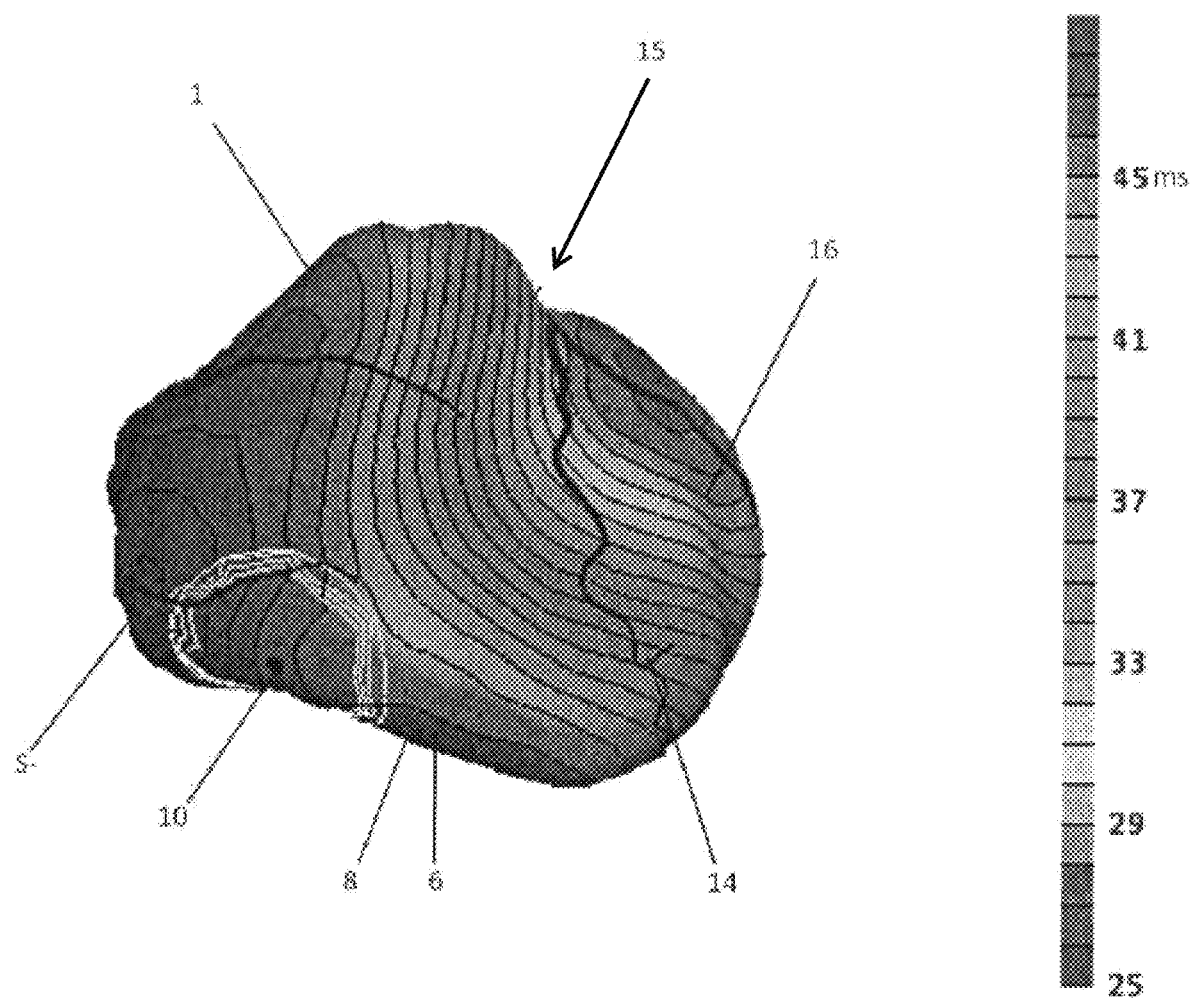
FIG. 2C is a plan view of a synchronicity map according to various embodiments.

FIGS. 2A-2D are 3D models 4 of a heart showing the initial electrical activation of a heart 1 from various single stimulation location 10. FIGS. 2A-2C show a ventricular surface of the myocardium with a septal wall 2. In general, the 3D model 4 may include a mesh 6 representing a ventricular surface of the heart, here an outer surface of the ventricular myocardium with septal wall as represented in FIG. 1. The mesh 6 has a plurality of nodes 8. In the illustrated example, the heart 1 is electrically stimulated at a stimulation location 10. Upon electrical stimulation at the stimulation location 10, the electrical signals will travel through the heart tissue. Hence, different parts of the heart will be activated at different times. Each location on the heart has a particular delay relative to the initial stimulation. Each node 8 has associated therewith a value representative of a time delay between stimulation of the heart 1 at the stimulation location 10 and activation of the heart at that respective node 8. Locations that share the same delay time are connected by isochrones 12 in FIGS. 2A-2D. In this application, isochrones are defined as lines drawn on a 3D heart surface model connecting points on the model at which the activation occurs or arrives at the same time. The delay time for nodes across the heart surface in this example is also displayed by differing rendering shading. The vertical bar indicates the time delay in milliseconds associated with the respective colors. It will be appreciated that the stimulation location 10 can be the location of intrinsic activation of the heart 1.

Figure 3:
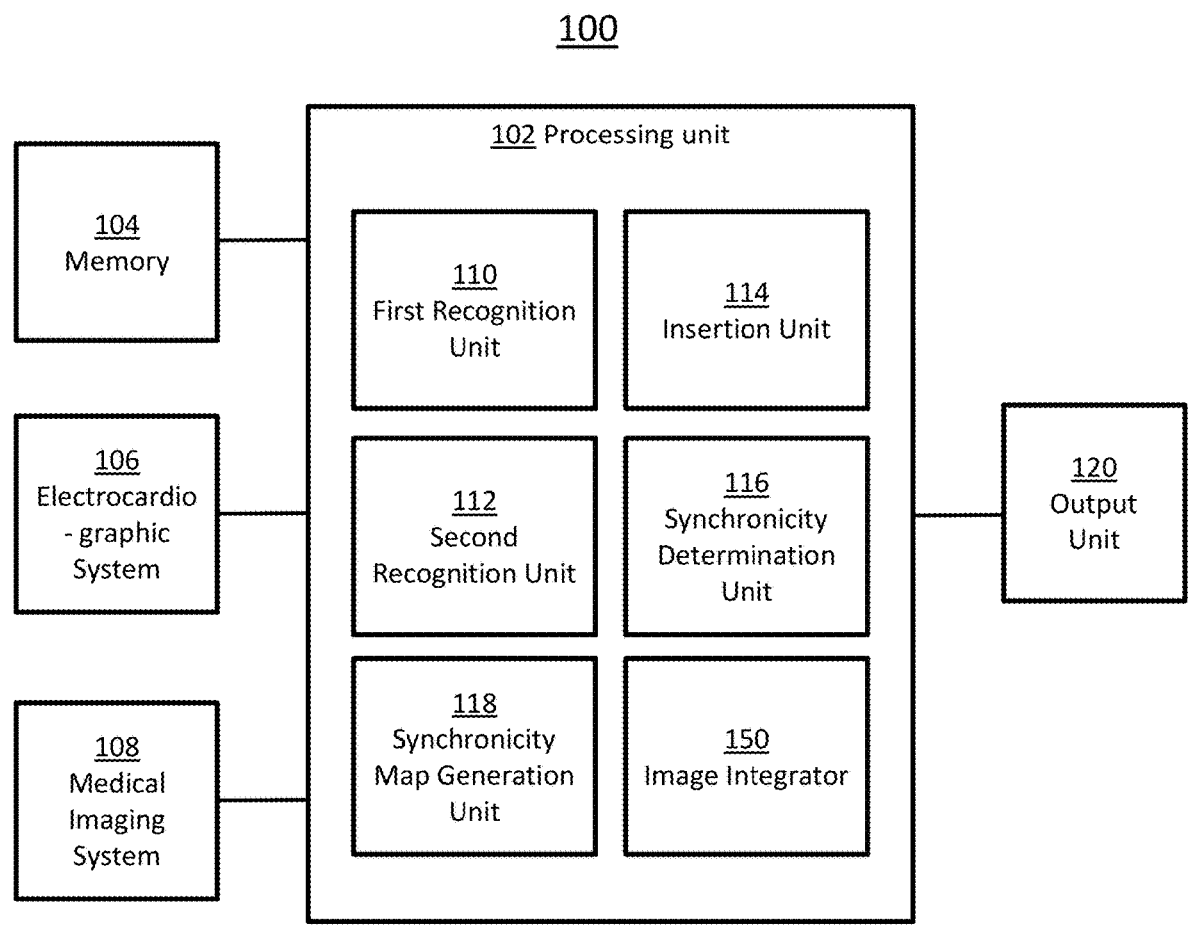
FIG. 3 is a schematic representation of a cardiac imaging system according to various embodiments.

FIG. 3 is a system block diagram of a system 100 for providing a representation of synchronicity of electrical activation of heart tissue. The system 100 includes a processing unit 102, and a memory 104.

The 3D electrical activation model 4 can be obtained by combining electrocardiographic and medical imaging data in a system 100. This data may be stored in the memory 104. The processing unit 102 may be connected to an electrocardiographic system 106 and a medical imaging system 108 for retrieving the data and storing corresponding data in the memory 104. An electrocardiographic imaging (ECGI) method able to determine the cardiac activation from a 12 lead ECG may be applied by the processing unit 102 for determining the 3D model 4 of electrical activation of the heart. In ECGI method, ECG signals may be combined with a patient-specific 3D anatomical model of the heart, lungs, and/or torso, in order to compute the positions of the cardiac isochrones. The patient-specific 3D anatomical model may be obtained from a magnetic resonance image (MRI) or computed tomography (CT) images received from a medical imaging system 108. Alternatively or additionally, a 3D anatomical model showing closest conformity to the patient may be selected, and optionally modified, from a database including a plurality of 3D anatomical models. The selected, and optionally modified, 3D anatomical model may serve as the patient-specific 3D anatomical model.

The 3D model 4 may also include further information. In the example illustrated in FIG. 2A, the 3D model 4 may include cardiac blood vessels 14 and/or veins on the myocardium. This information may be added to the 3D model 4 in that nodes are indicated as being associated with such blood vessel. The blood vessels 14 may then be identified and optionally shown in the 3D model 4. Optionally, the processing unit 102 may include a first recognition unit 110 arranged for automatically retrieving information representative of the location of such blood vessels from the patient's 3D anatomical model of the heart. The processing unit 102 may then automatically insert this information into the 3D model 4.

The 3D model 4 may also include information on scar tissue. Scar tissue locations may be obtained from delayed enhancement magnetic resonance imaging (MRI) images and added to the 3D model 4. Scar tissue can be simulated in the 3D model 4 by reducing the propagation velocity of electrical signals there through. Scar tissue can also be accounted for by setting the transition from one node to another to very slow or non-transitional for the areas in the heart wall where scar tissue is present. Optionally, the processing unit 102 may include a second recognition unit 112 configured and arranged for automatically retrieving information representative of the location of such scar tissue from the patient-specific 3D anatomical model of the heart. The processing unit 102 may automatically insert this information into the 3D model 4.

In various embodiments, the obtained 3D model 4 may be used for obtaining further information on electrical activation of the heart. For example, the time delay of activation from one node to another may be determined. This may be used to generate, on the basis of the 3D model 4, other views resulting from initial stimulation at other nodes of the mesh 6. To enable this, the processing unit 102 may include an insertion unit 114, which may take the 3D model 4 and define a certain node as a stimulation location. It will be appreciated that the 3D model 4 may assume stimulation at a predetermined node. The insertion unit 114 may remove stimulation at that predetermined node for calculation purposes.

FIG. 2B shows an example 3D model 4 resulting from initial stimulation at another stimulation location 10'. It will be appreciated that a view resulting from initial stimulation at other nodes of the mesh 6 may be generated for each node of the mesh 6.

A particular electrical activation sequence of the entire heart 1, resulting from stimulation at a particular node, may be summarized in a single parameter, namely, heart activation synchronicity. The heart activation synchronicity provides an indication of how synchronously the entire heart is activated. For common situations, a more synchronous activation of the heart is considered beneficial. The measure for heart activation synchronicity in this example is the standard deviation (std) of the depolarization (dep) times of the heart. Hence, the heart activation synchronicity provides an indication of synchronicity of activation of the entire heart as a result of stimulation at the respective node. The processing unit 102 may include a synchronicity determination unit 116 configured to determine the heart activation synchronicity.

In various embodiments, the heart activation synchronicity may be determined separately for stimulation at each node. Hence, a measure of heart activation synchronicity for each node of the mesh may be provided. The processing unit 102 may include a synchronicity map generation unit 118 configured to generate a synchronicity map based on the calculation of the heart activation synchronicity for each node, by the synchronicity determination unit 116. The processing unit 102 may be connected with an output unit 120 arranged for outputting the synchronicity map 15 and/or alternative data to a user. The output unit may be a display unit, a printer, a messaging unit, or the like.

Figure 2D:
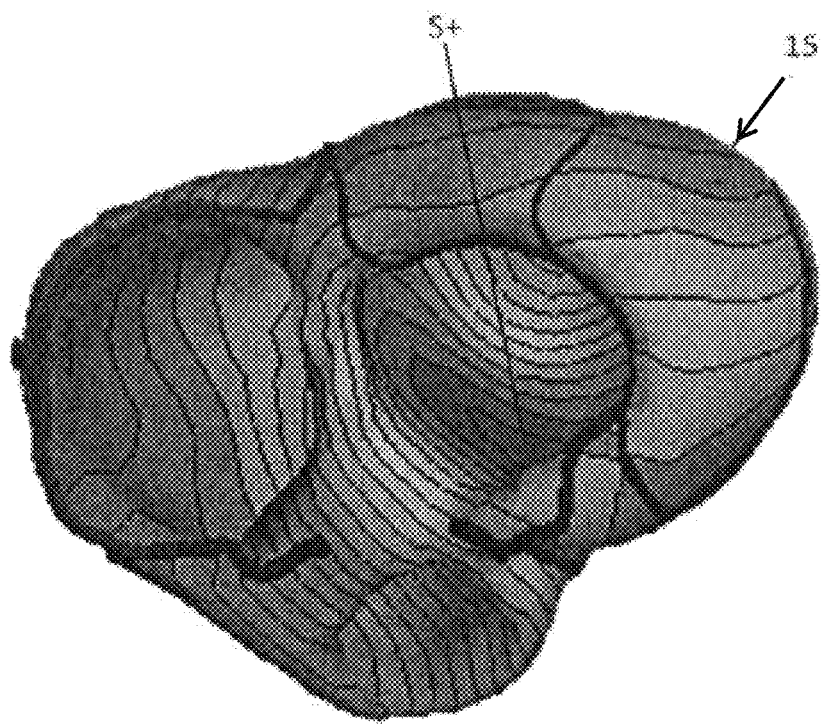
FIG. 2D is a plan view of a synchronicity map according to various embodiments.

FIG. 2C shows an example of a heart synchronicity map 15. In the example illustrated in FIG. 2C, heart activation synchronicity is indicated for each node in the map 15. In this example, the indication may be shown by providing false colors and/or iso-sync lines 16. The iso-sync lines 16 connect nodes having the same heart activation synchronicity. The heart synchronicity map 15 provides a singular 3D overview showing the locations on the heart that result in good heart activation synchronicity, and the locations on the heart that result in poor heart activation synchronicity, if the heart were stimulated at such locations. In the example illustrated in FIG. 2C, it can be seen that the original stimulation location 10 does not provide particularly good synchronization, with a heart activation synchronicity value of approximately 45 ms standard deviation of the depolarization times of the heart. The least favorable stimulation location, here the location with the highest heart activation synchronicity value, is indicated at S–. In this example, the most favorable stimulation location, where the lowest heart activation synchronicity value occurs, is indicated at S+. In some instances, the most favorable stimulation location S+ can best b e seen when looking at the synchronicity map 15 from another direction, as shown in FIG. 2D.

Another example of a measure for heart activation synchronicity is a range in depolarization times (maximum depolarization time–minimum depolarization time). The range in depolarization times may be corrected for cycle length. Another example of a measure for heart activation synchronicity is a standard deviation of the Left Ventricle (LV) depolarization times only. Another example of a measure for heart activation synchronicity is a delay between stimulus and Septum activation. Another example of a measure for heart activation synchronicity is an AV delay. Another example of a measure for heart activation synchronicity is a VV delay. It will be appreciated that the measure for heart activation synchronicity may be chosen depending upon the task at hand and/or depending on a specific condition or abnormality experienced in the patient.

Figure 4A:
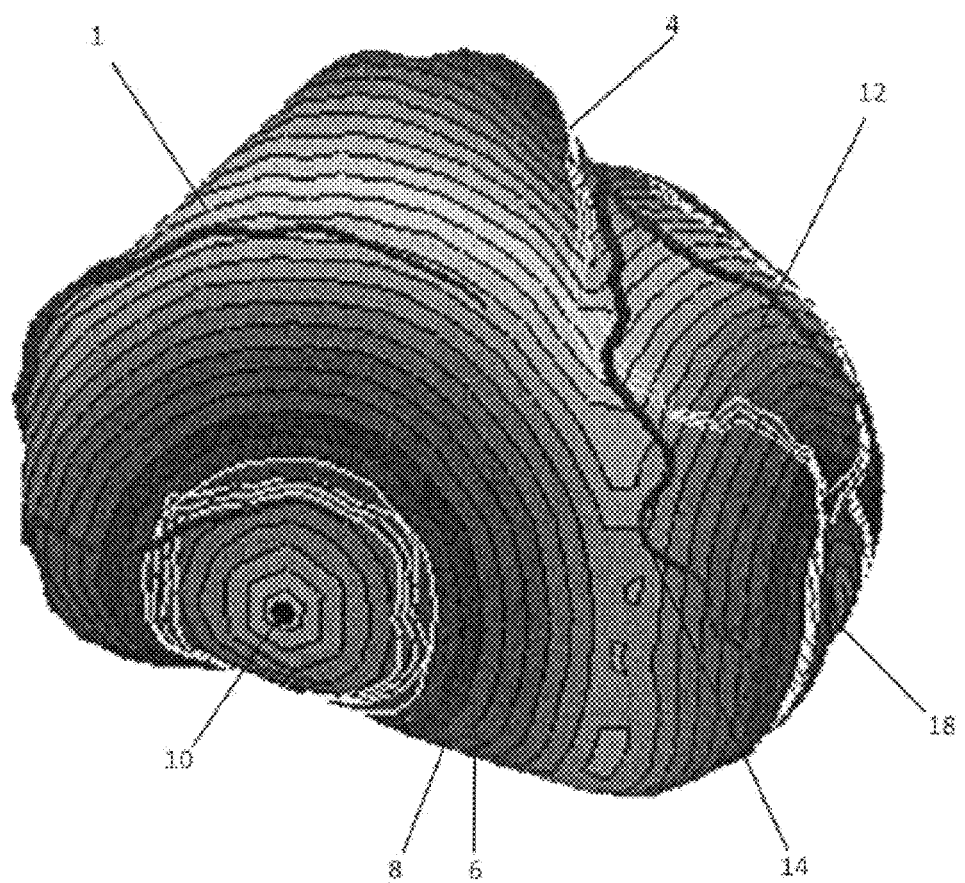
FIGS. 4A and 4B are plan views of 3D models of the electrical activation of a heart according to various embodiments.

FIG. 4A shows a second example in which a second stimulation location 18 is defined. Electrical activation of the heart is calculated using the 3D model 4 and simultaneous stimulation at the first stimulation location 10 and the second stimulation location 18. In this example, the insertion unit 114 does not remove stimulation at the first location 8 for calculation purposes. FIG. 4A shows the calculated resulting electrical activation of the heart 1. In the example illustrated in FIG. 4A, the total activation time shortens due to the addition of the second stimulation location 18. In this example, the first stimulation location 10 represents the location of intrinsic activation of the heart, or a first chosen location to stimulate or a stimulation generated by an already present pacemaker lead within the heart.

Figure 4B:
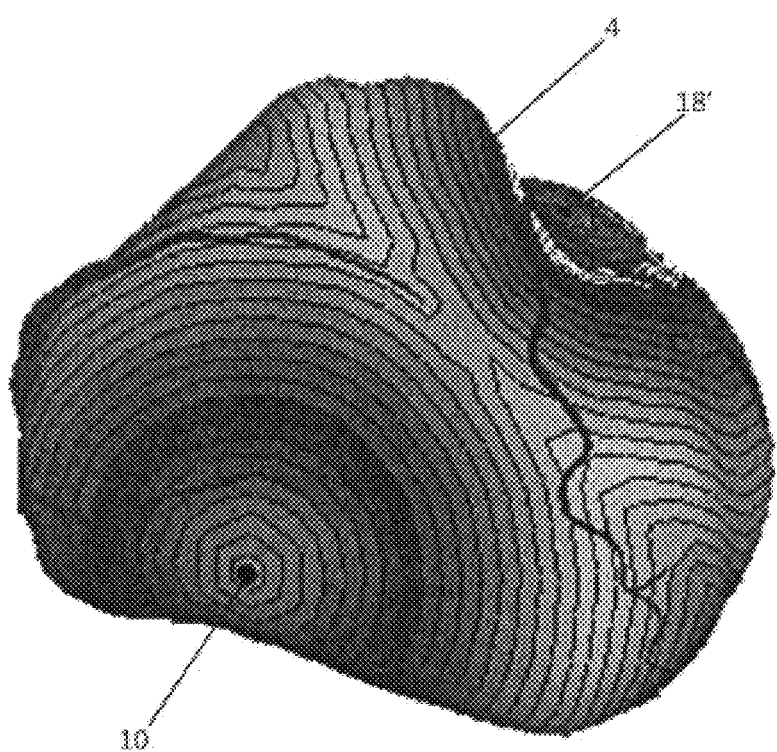

FIG. 4B shows an example of electrical activation of the heart resulting from initial stimulation at a second stimulation location 18' simultaneous with stimulation at first stimulation location 10. It will be appreciated that a view resulting from initial stimulation at second nodes of the mesh 6, simultaneous with stimulation at a first node associated with the first stimulation location 10 may be generated for each node of the mesh 6.

Figure 4C:
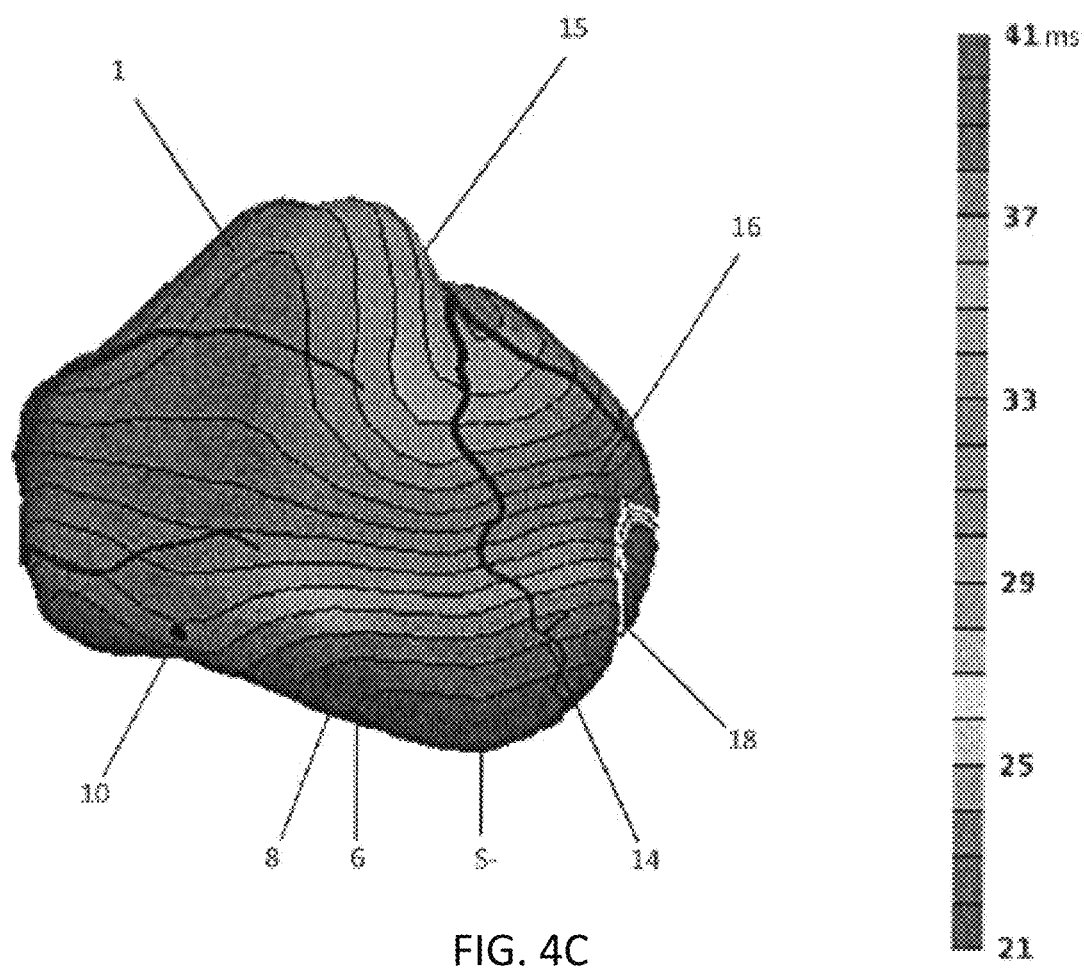
FIGS. 4C and 4D are plan views of synchronicity maps according to various embodiments.
Figure 4D:
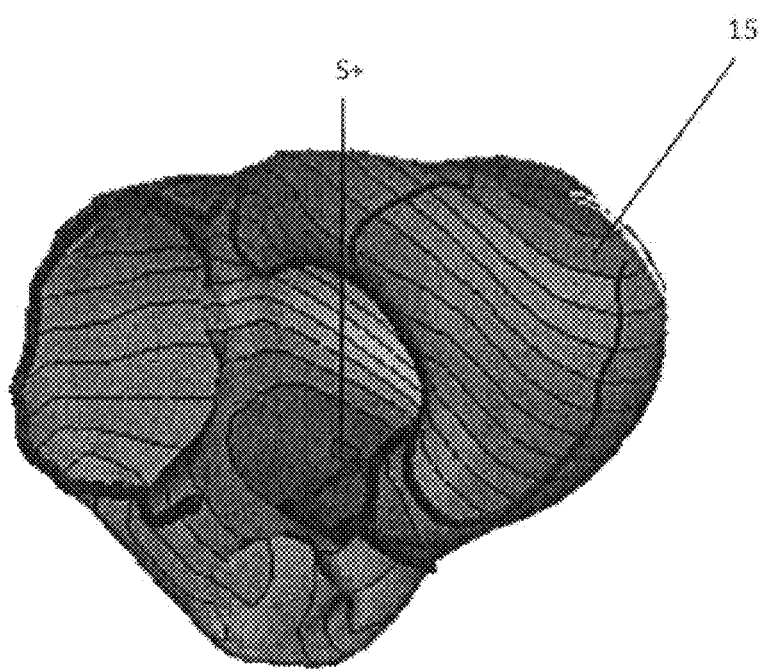

In the example illustrated in FIGS. 4C and 4D, a particular electrical activation sequence of the entire heart is combined and shown as the heart activation synchronicity. In this example, the electrical activation sequence involves stimulation at the second stimulation location 18 at the same time as stimulation at the first stimulation location 10. The heart activation synchronicity again provides an indication of how synchronously the entire heart is activated. In some embodiments, the heart activation synchronicity may be determined separately for stimulations at each node simultaneously with stimulation at the first 10 and second 18 stimulation locations. This provides a measure of heart activation synchronicity for each node acting as a third stimulation location of the mesh 6.

FIG. 4C shows an example of a heart synchronicity map showing locations on the heart that result in good heart activation synchronicity as well as location on the heart that result in poor heart activation synchronicity if the heart were stimulated at such locations simultaneous with stimulation at the first stimulation location 10 and the second stimulation location 18. In the example illustrated in FIG. 4C, the least favorable third stimulation location S– had the highest heart activation synchronicity value of approximately 41 ms, when the first stimulation location 10 and the second stimulation location 18 were stimulated simultaneously. In this example, the most favorable third stimulation location S+ had the lowest heart activation synchronicity value, when with the first stimulation location 10 and the second stimulation location 18 were stimulated simultaneously. In some circumstances, the most favorable stimulation location S+ can best be seen when looking at the synchronicity map 15 from another direction, as shown in FIG. 4D.

Figure 5:
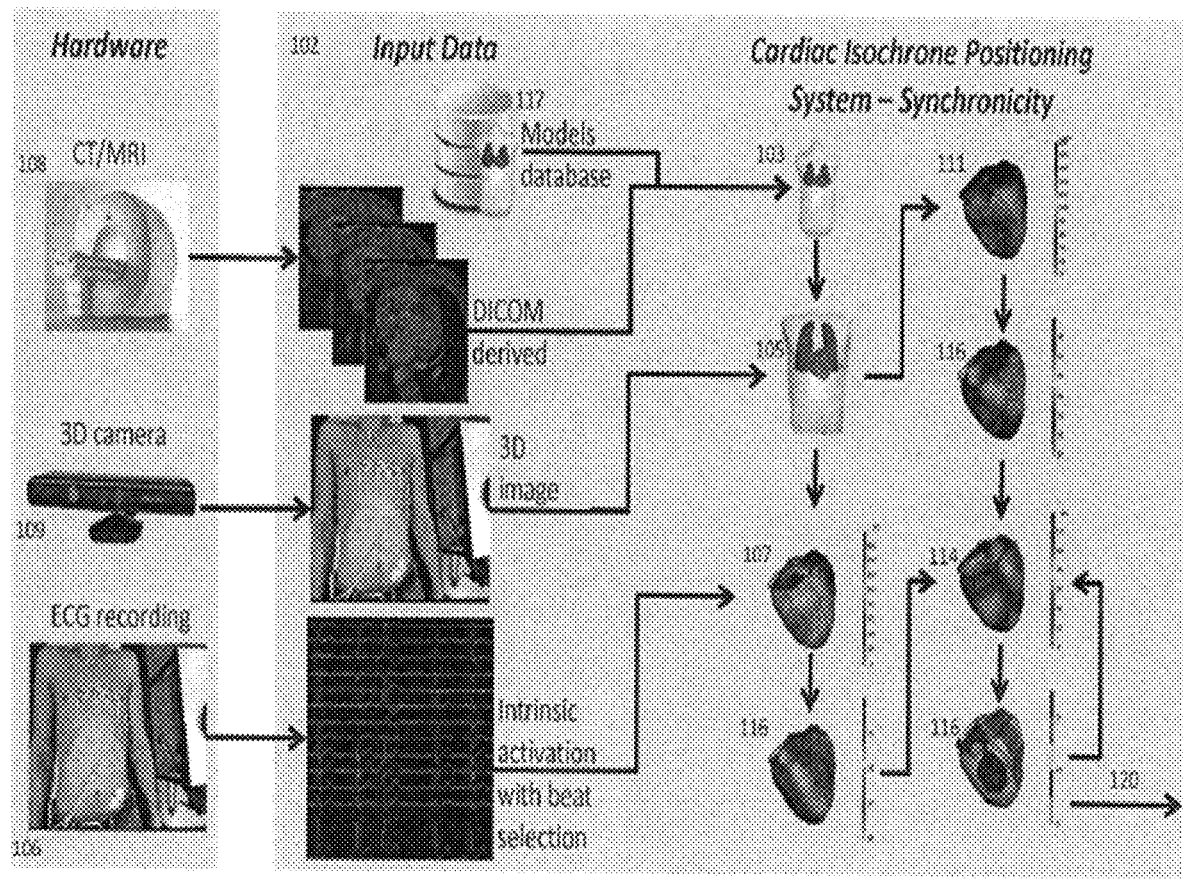
FIG. 5 is a schematic representation of a cardiac imaging system according to various embodiments.
Figure 6:
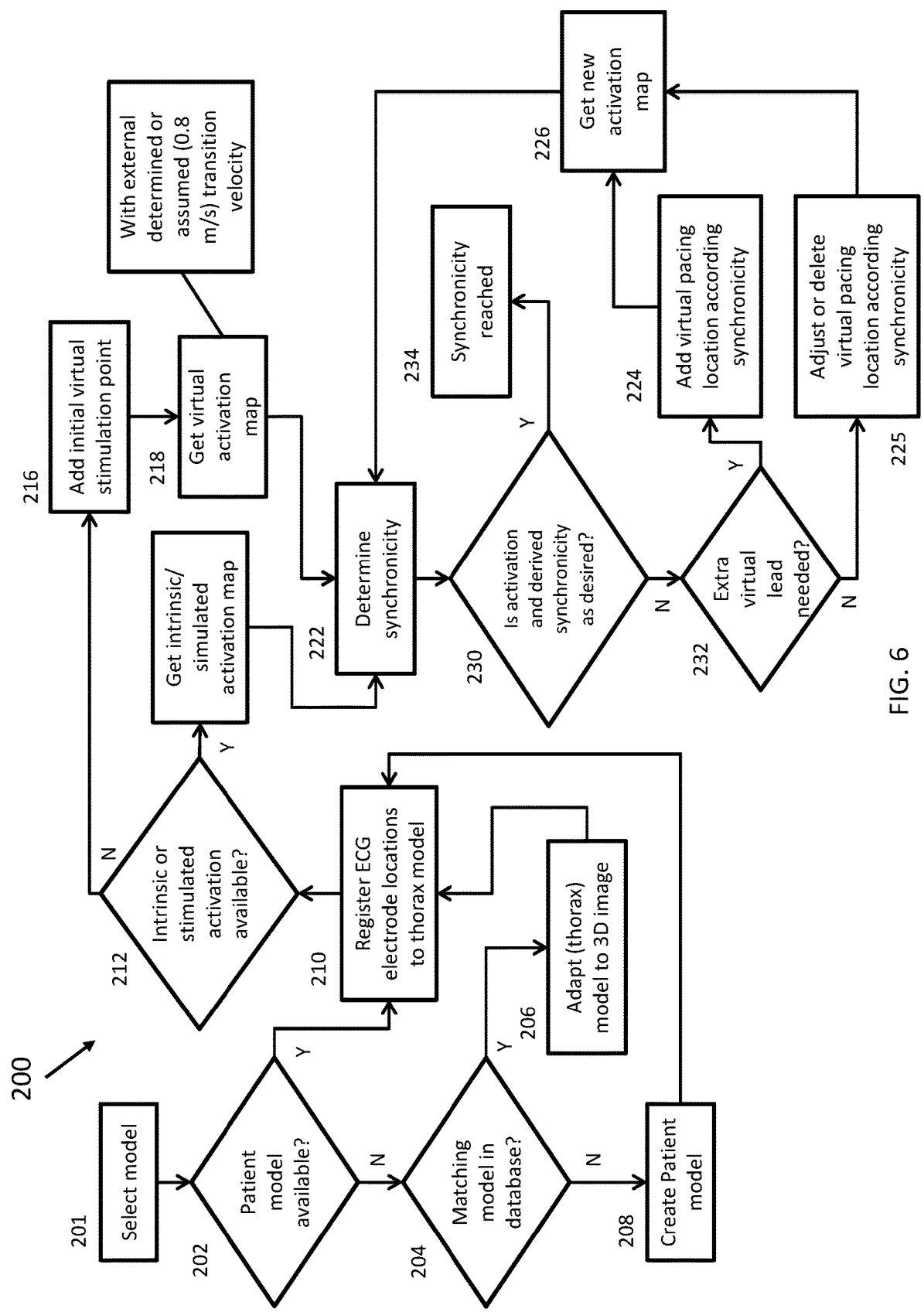
FIG. 6 is a flow chart illustrating a method according to various embodiments.

FIG. 5 is a data flow representation of a system 100 for providing a synchronicity map. FIG. 6 illustrates a method of determining heart synchronicity using the system 100 illustrated in FIGS. 3 and 5 according to an embodiment. Referring to FIGS. 3 and 5, the system 100 includes a processing unit 102 which receives data from hardware modules. Optionally the processing unit 102 may receive ECG data from an electrocardiographic system 106. The processing unit may receive patient-specific anatomical data from a medical imaging system 108.

The processing unit 102 may receive information on the positions of ECG leads relative to the anatomy of the patient from a positioning system 109, such as a 3D image of a patient's chest including the electrodes. The 3D image and the torso model may be aligned, and the locations of the electrodes in the model may be adjusted to coincide with the electrode locations in the 3D image. Knowledge of the location of the ECG electrodes relative to the heart, and in particular the V1-6 precordial electrodes, may be especially important for accurately computing the onset location of PVC.

In some embodiments, the offsets of the electrodes from their assumed ideal locations, and in particular offsets of the V1-6 electrodes, may be determined based on a comparison of detected ECG signals of a normal heart beat to ideal ECG normal heart beat signals. For example, the offsets may be determined based on how a detected ECG signal will be affected by variations in the position of electrodes with respect to ideal electrode positions. In particular, the recorded ECG data may be used to determine a stimulation onset location for a normal beat. Since the normal onset location in the SA node is known, the determined offset location may be compared to this known onset location, and the offset of the electrodes may be deduced based on the variation therebetween. As such, it may be possible to determine electrode offsets without generating the 3D map.

From the patient-specific anatomical data, the processing unit 102 may determine the synchronicity map 15. The processing unit 102 may include the following units, and may perform the operations of the method 200 illustrated in FIG. 6 and described below to generate a synchronicity map. In the method 200, the processing unit 102 may use a patient-specific 3D anatomical model of the thorax of the patient and the size, orientation, and location of the size, orientation, and location of the heart within the thorax. Such a model may be selected in block 201 for further use by the processing unit 102. The processor may determine whether such a model is already available in determination block 202. If the model is not yet available (i.e., determination block 202=N), a retrieval unit 103 may check whether a suitable anatomical model for this patient is present in a database 117 in determination block 204.

If no suitable patient-specific anatomical model is available in the database 117 (i.e., determination block 202=N), the retrieval unit 103 may generate the patient-specific anatomical model on the basis of the received patient-specific anatomical 3D image data in block 208.

If a suitable patient-specific anatomical model is available in the database 117 (i.e., determination block 202=Y), the retrieval unit 103 retrieves the suitable anatomical model from the database 117 in block 206. Also in block 206, the retrieval unit 103 may adapt the anatomical model from the database to the 3D image of the patient, so as to transform the selected anatomical model into a (quasi) patient-specific 3D anatomical model. Optionally, the patient-specific 3D model may also include the size, orientation and/or location of other structures in the patient, such as the lungs and/or other organs. The patient-specific 3D model may be a volume conductor model.

If a patient model is available (i.e., determination block 202=Y), or using a patient model created in block 208 or a stored model adapted to the patent in block 206, the positions of ECG leads and the patient-specific model, a lead locator module 105 may determine corresponding positions of the ECG leads in the patient-specific 3D model to provide an enhanced patient-specific model in block 210.

In determination block 212, when the patient-specific anatomical model and/or the enhanced patient-specific model available, a determination is made as to whether ECG data representative of intrinsic or stimulated activation is available. If intrinsic activation data or pacing stimulation from one or more already present pacemaker leads is available (i.e., determination block 212=Y), an activation unit 107 may generate a 3D electrical model of showing the current activation of the heart of the patient on the basis of the patient-specific model and the ECG data in block 214.

If no ECG data on intrinsic or stimulated activation is available (i.e., determination block 212=N), a virtual stimulation unit 111 may add an initial virtual stimulation to an electrical model of the heart, based on previously determined and/or assumed transition velocities between nodes, in block 216. An assumed transition velocity may be 0.8 ms, for example. The electrical model may include arteries, veins, and/or scar tissue as explained above. In block 218, a 3D electric model of virtual activation of the heart of the patient may be generated.

From the 3D electric model of intrinsic, stimulated, or virtual activation of the heart of the patient, a synchronicity determination unit 116 may generate a synchronicity map 15 in block 222, as described above. On the basis of the synchronicity map, the processing unit 102 may determine whether the artificial stimulation location or virtual stimulation location resulted in optimal activation and synchronicity in determination block 230. If so (i.e., determination block 230=Y), the processing unit may calculate optimal stimulation locations for a patient's heart in block 234.

If it is determined in block 230 that optimum synchronicity has not been reached (i.e., determination block 230=N), the method 200 proceeds to determination block 232 in which it is determined whether an extra virtual stimulation location is needed or should be added, or if a virtual stimulation location should be moved or changed with respect to the timing parameters. This determination may be made by a clinician, by the processing unit, or by the clinician based on information or recommendations presented on a display by the processing unit.

If it is determined that an extra virtual lead is needed (i.e., determination block 232=Y), a virtual pacing location may be added according to the determined synchronicity in block 224. If it is determined that an extra virtual lead is not needed and a virtual stimulation location should be moved or changed (i.e., determination block 232=N), the artificial or virtual stimulation location may be adjusted accordingly in block 225.

In block 226, a new activation may be generated. Synchronicity may then be recalculated in block 222, and the process may be repeated until a desired activation is determined to be achieved in determination block 230.

The system 100 may also virtually adapt the current artificial stimulation locations, i.e., pacemaker lead locations, with respect to its current stimulation parameters to reach optimum synchronicity.

The system 100 may also be used for assessing multiple stimulations. For example, the multiple stimulations may be a combination of intrinsic activation and stimulated activation (pacing). For example, the multiple stimulations may be a multiple stimulated activation (pacing). It is possible that the user or the processing unit 102 determines 232 whether an additional stimulation location, such as an additional pacemaker lead, would be desirable.

If an additional stimulation location is desired, an additional stimulation location may be inserted by the insertion unit 114. Then, activation for the situation with the original stimulation location and the added virtual stimulation location may be determined again in block 226, and synchronicity may be recalculated in block 222. On the basis of the synchronicity map, the processing unit 102 may determine in determination block 230 whether the additional virtual stimulation location resulted in optimum synchronicity. If the optimum synchronicity has not been reached, the method 200 proceeds to block 232, in which it is determined whether an extra virtual stimulation location should be added, or if a virtual stimulation location should be moved or removed, with respect to the timing parameters. In such a case, the process may be repeated one or more times.

Based on the patient specific cardiac activation model, a cardiac synchronicity model may be generated. The synchronicity model may be a 3D heart surface model including iso-sync lines as described above in which the iso-sync lines represent the activation synchronicity of the heart. This synchronicity may be based on specific activation conditions, such as right ventricle activation at a lead position of a pacemaker.

As an example, the synchronicity model may be generated and the activation isochrones for the intrinsic LBBB pattern may be determined in the following blocks.

1A) A patient-specific anatomical 3D model of the heart, lungs, and thorax may be generated, e.g. on the basis of an MRI or CT image of the patient, or derived from a model taken from a database adapted to the patient's dimensions, e.g. with use of the 3D camera. The anatomical 3D model may include a 3D surface model of the heart, a 3D surface model of the lungs, and a 3D surface model of the thorax. A 3D surface model may be a close approximation of the actual surface of the heart by means of a mesh of a plurality of polygons, such as triangles, connected at their corners. The interconnected corners form nodes of the mesh.

1B) An ECG, e.g. a 12-lead ECG, may be measured. The exact locations of the electrodes of the ECG device on the thorax may be recorded. The positions of the electrodes in the 3D anatomical model are used for estimating the distribution, fluctuation, and/or movement of electrical activity through heart tissue. The exact locations of the recording leads or the ECG device may be entered in the anatomical 3D representation of the thorax.

1C) Optionally, scar tissue may be incorporated in the anatomical 3D representation of the heart. The presence and location of scar tissue may be derived from delayed enhancement MRI images.

1D) The measurements per recording lead of the ECG device may be related to the heart and torso geometry. Using an inverse procedure, the intrinsic activation may be determined. The distribution, fluctuation, and/or movement of electrical activity through heart tissue may be based upon a myocardial distance function, a fastest route algorithm, shortest path algorithm, and/or fast marching algorithm.

2) Once the activation isochrones for the intrinsic LBBB pattern have been determined, a stimulus site may be added to the intrinsic activation for each node on the heart and the desired synchronicity of the heart may be computed from the outcome. A "node" refers to an intersection point of the triangles of upon which the anatomical 3D heart model is based.

The above methods may also be used to determine an optimal location for placement of a cardiac pacemaker electrode. To determine the optimal pacing site, synchronicity maps may be computed. The intrinsic activation map, in combination with a determined stimulation point may be applied to a new cardiac isochrone positing map.

Figure 7A:
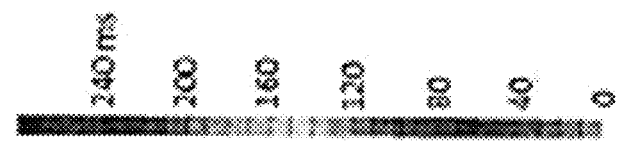
FIG. 7A is schematic representations of LAO and PA views of a 3D model of electrical activation of a heart according to various embodiments.
Figure 7A:
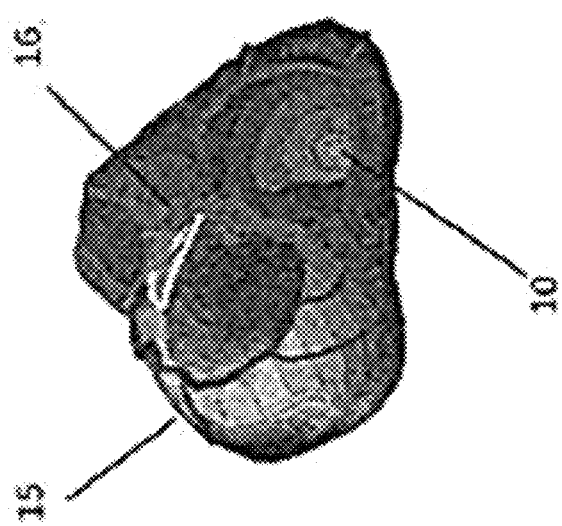
Figure 7A:
Figure 7A:
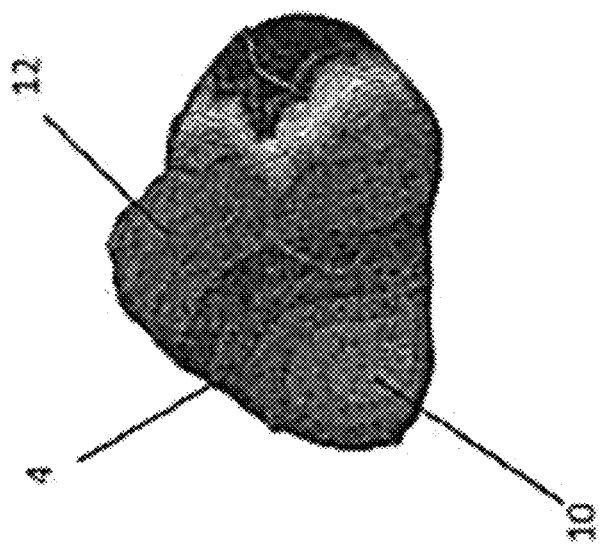
Figure 7B:
FIG. 7B is schematic representations of LAO and PA views of a synchronicity map according to various embodiments.
Figure 7B:
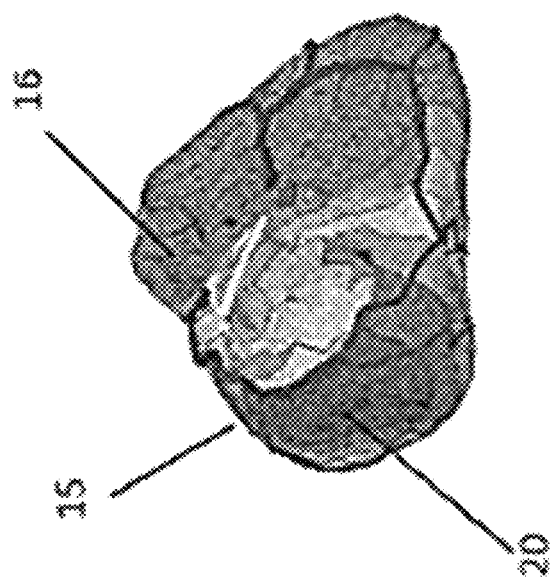
Figure 7B:
Figure 7B:
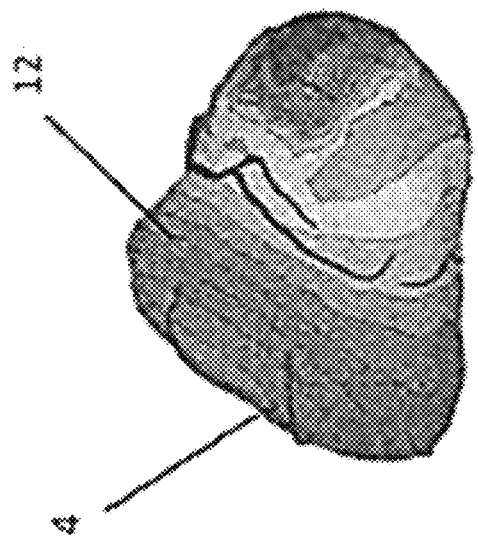

FIG. 7A shows examples of 3D synchronization maps of LBBB activation patterns of a heart. On the left, FIG. 7A shows the left anterior oblique (LOA) view. On the right, FIG. 7A shows a postero-anterior (PA) view. FIG. 7B shows a synchronization map for the heart of FIG. 7A. On the left, FIG. 7B shows the LAO view and on the right, FIG. 7B shows the PA view.

The synchronicity map of FIG. 7B shows the standard deviation of the depolarization times of the heart as a result of one extra stimulation location combined with the intrinsic activation of the heart. From FIG. 7B, it can be seen that choosing an additional stimulation location on the basal left free wall 20 reduces the standard deviation of the depolarization times of the heart the most. Therefore, in this example the area on the basal left free wall could be selected as best location for a pacemaker electrode.

An updated 3D model of electrical activation of the heart may be generated including intrinsic activation simultaneously with stimulation in the area on the basal left free wall. This updated 3D map may then be used to generate a new synchronicity map to check the lead location(s) in the RV. By doing this, a clinician may determine whether lead(s) should also stimulate instead of only sensing. A clinician may also determine whether lead(s) should be shifted. A clinician may also determine whether extra stimulation lead(s) should be added.

A clinician may also determine whether intrinsic AV conduction is beneficial. Intrinsic AV conduction will generally conduct to the right bundle, after which the LV needs to be activated by stimulating the LV. This may also be reversed, i.e., with a RBBB waiting for LV activation and stimulating the RV free wall at an optimal position. By repeating the procedure for both left and right ventricle, the exact location and timing of cardiac pacing can be fine-tuned.

When the intrinsic activation signal is not usable due to severe damage of the heart, the whole procedure may be performed using only simulated (pacemaker) stimulation, instead of the intrinsic activation. Blocks 1B and 1D above may be omitted in that case. The whole procedure will then be based on artificial activation.

Figure 8A:
FIG. 8A is schematic representations of LAO and PA views of a 3D model of electrical activation of a heart according to various embodiments.
Figure 8A:
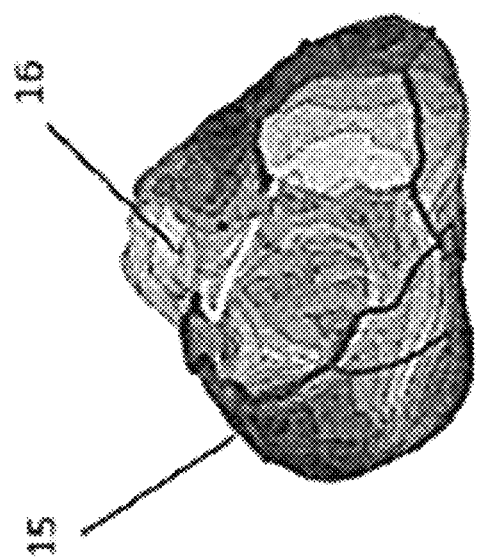
Figure 8A:
Figure 8A:
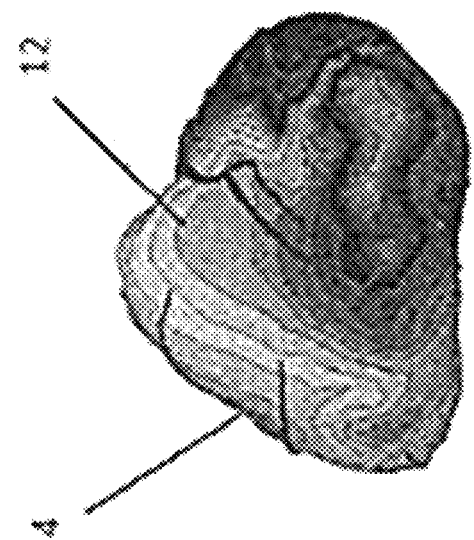
Figure 8B:
FIG. 8B is schematic representations of LAO and PA views of a synchronicity map according to various embodiments.
Figure 8B:
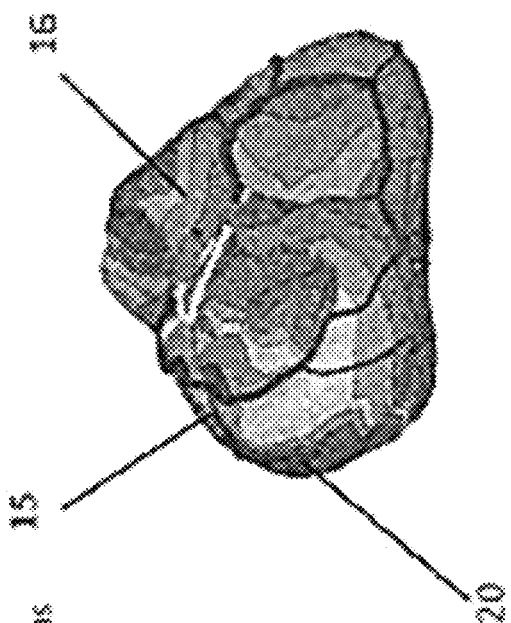
Figure 8B:
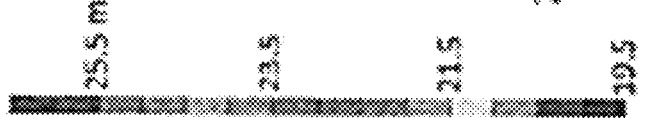
Figure 8B:
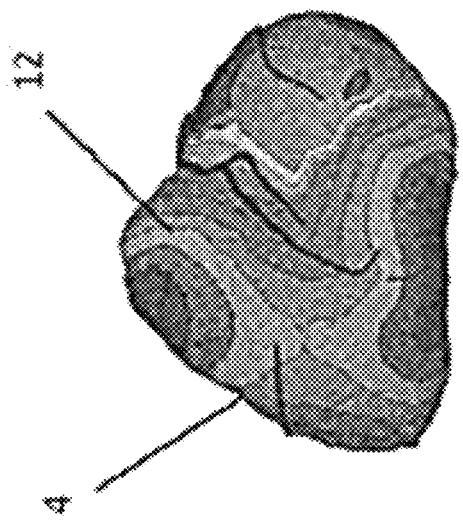

FIG. 8A shows an example of left stimulated activation of an LBBB pattern. On the left FIG. 8A shows the LAO view, on the right the PA view. FIG. 8B shows an example of a synchronicity map 15 for the heart shown in FIG. 8A. On the left FIG. 8B shows the LAO view, on the right the PA view. The synchronicity map of FIG. 8B shows the standard deviation of the depolarization times of the heart as a result of one extra stimulation location combined with the left stimulated activation of the heart. From FIG. 8B, it can be seen that choosing the additional stimulation location in the area on the basal left free wall 20 reduces the standard deviation of the depolarization times of the heart the most. Therefore, in this example the area on the basal left free wall could be selected as best location for a pacemaker electrode. An updated 3D model of electrical activation of the heart may be generated including intrinsic activation simultaneously with stimulation in the area on the basal left free wall.

The whole procedure described above may be performed during the implantation procedure to find most optimal pacing sites.

Figure 9:
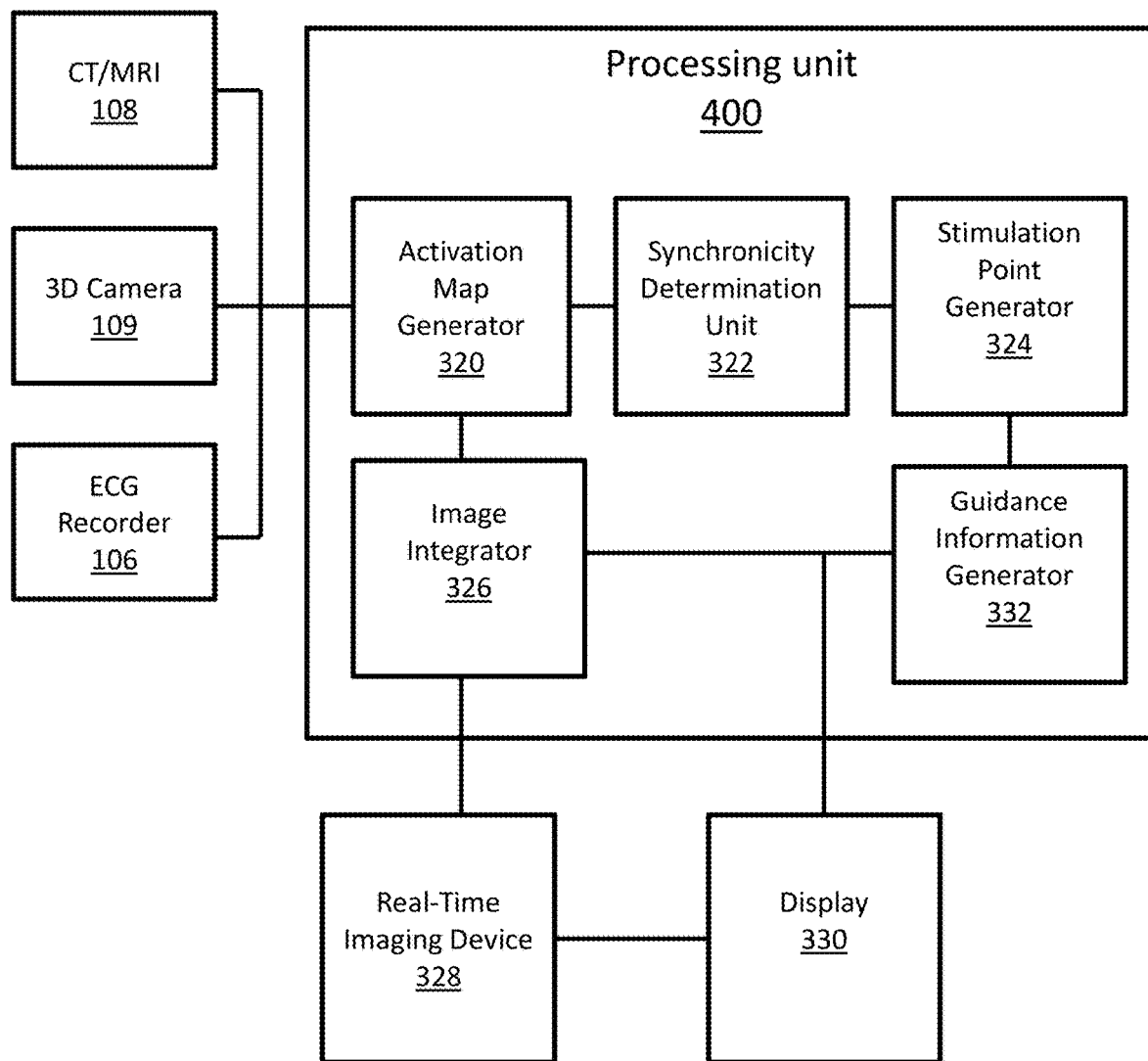
FIG. 9 is a schematic diagram of a surgical imaging system according to various embodiments.
Figure 10:
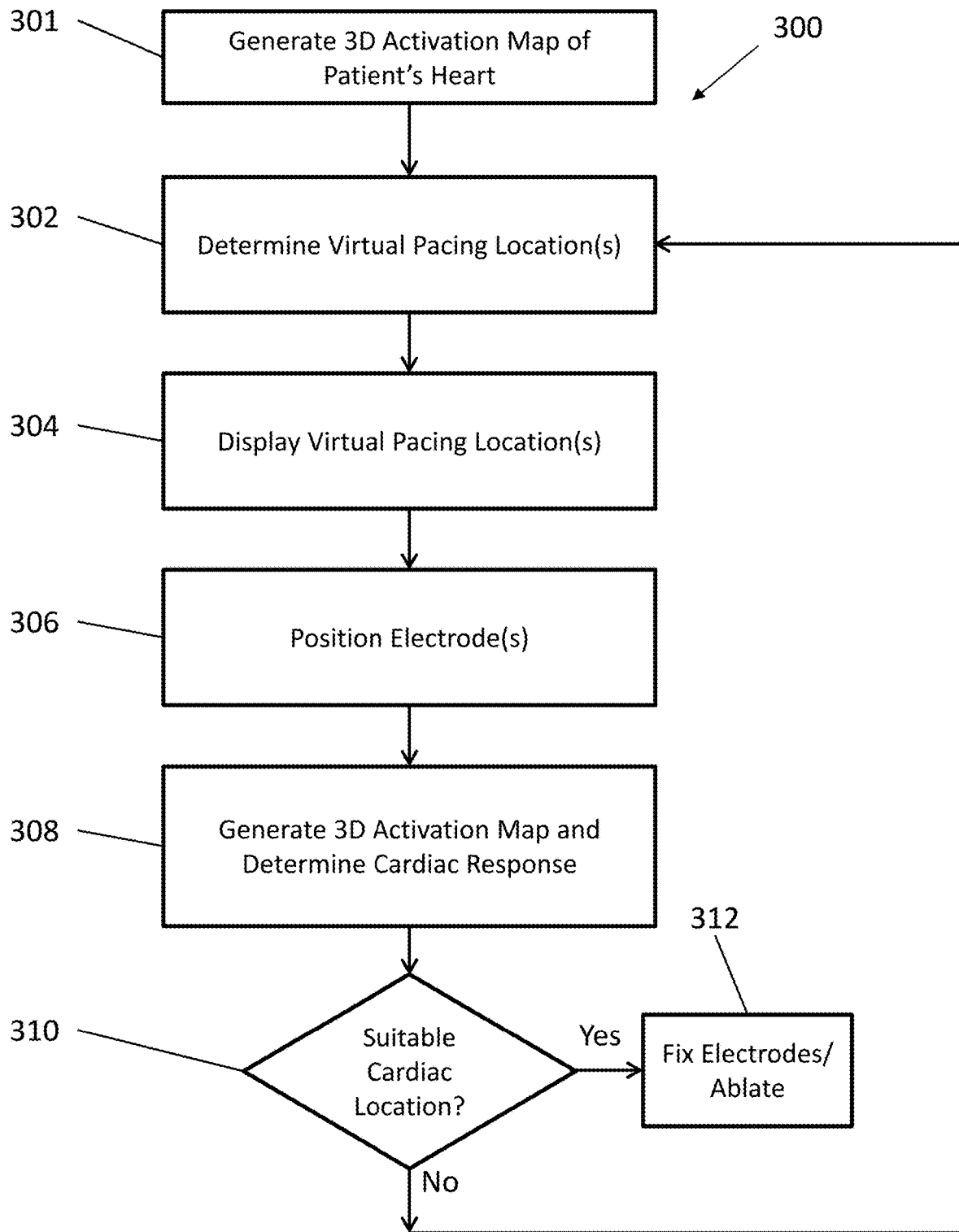
FIG. 10 is a flow diagram of a method of using the system of FIG. 9 according to various embodiments.

FIG. 9 is a block diagram of a cardiac imaging system according to various embodiments. FIG. 10 is a flow diagram showing a method 300 of implanting an electrode using the system of FIG. 9, according to various embodiments. Referring to FIGS. 9 and 10, in block 301, a 3D activation map of the heart of a patient may be generated by a processing unit 400 of the system. In particular, a 3D model of the chest and/or heart of the patient may be generated by a CT or MRI device 108, ECG data of the patient may be recorded by an ECG recorder 106, and a 3D image of the torso of the patient may be generated by a 3D camera 109. This data may be provided to an activation map generator 320 of the processing unit 400. The ECG data may include extrinsic and/or intrinsic stimulation signals received from the patient.

In block 302, the locations of one or more predicted optimal pacing locations may be identified. For example, the activation map may be provided to a synchronicity determining unit 322 to determine cardiac synchronicity. This data may then be used by a virtual stimulation point generator 324 to identify one or more suggested pacing locations.

In CRT patients, pacing locations may be located in positions where cardiac dyssynchrony occurs, such that the stimulation thereof is predicted to generate maximized amounts of heart activation and/or synchronization. The pacing locations may be based on a difference between LV and RV activation times, earliest and/or latest activation of the LV and/or RV, a detected depolarization wave blockage, or the like, for example.

In block 304, one or more virtual pacing locations may be displayed. For example, one or more pacing locations may be added to the activation map as virtual pacing locations. In the alternative, the activation map and images generated by a real-time imaging device 328, such as a fluoroscope, a radiography device, an X-ray computed tomography (CT) device, or the like, may be provided to an image integrator 326. The image integrator 326 may compare and/or align the activation map and the real-time image. Based on the comparison and/or alignment, the activation map including the stimulation point(s) may be overlain on the real-time image. In other embodiments, virtual stimulation point(s) may be added to the real-time images to produce modified real-time images that may be provided to a display 330 for rendering.

In some embodiments, in addition to displaying the activation map, block 304 may include providing a reference image showing internal structures of the heart to the display 330. The additional image may be based on a 2D cardiac image, such as one of the MRI or CT images used to generate the activation map. Such a 2D image may be modified to show additional features. For example, a 2D cardiac image may be modified to identify structures included in an area of earliest activation and/or pacing location(s) included in the activation map. Accordingly, the reference image could be referred to when positioning electrodes using the real-time imaging device 328. Reference images are discussed in detail below with reference to FIG. 11B.

In block 306, one or more pacing electrodes may be positioned at the identified virtual stimulation point(s). A physician may use the reference image and or the activation map shown in the display 330 to align a pacing electrode with the virtual stimulation point. The heart may then be paced, and the resulting ECG data may be collected.

In block 308, the collected ECG data may be used to generate an updated activation map to show the effect of the stimulation. In some embodiments, the ECG data may be used to identify the pacing location, which may be displayed on the activation map. Since the pacing electrode is disposed at the pacing location, the pacing location may represent the current location of the pacing electrode. Accordingly, pacing electrode locations may be displayed while navigating to a pacing location. As such, additional mapping applications may not be needed for determining the location of a pacing electrode, thereby substantially reducing costs of a pacing procedure.

In determination block 310, a determination may be made whether a pacing electrode is disposed in a suitable cardiac location. For example, in CRT patients, it may be determined whether stimulation at a cardiac location resulted in a sufficient amount of synchronicity and/or restored a desired amount of heart function. If so (i.e., determination block 310=Yes), the electrodes may be sutured in place in block 312. If not (i.e., determination block 310=No), new cardiac stimulation point(s) may be generated in block 302, based on the updated activation map generated in block 308. For example, one or more virtual stimulations points may be moved to new locations, and/or additional virtual stimulation points may be added. The virtual stimulation points may then be added to the real-time cardiac image in block 304. In some embodiments, the pacing interval at which the LV and RV are stimulated may also be adjusted.

For PVC and/or VT patients, determination block 310 may include using the updated activation map to determine whether the stimulation replicates the patient's PVC. In other words, determination block 310 may include determining whether the stimulation point is a suitable ablation point. If so (i.e., determination block 310=Yes), the heart may be ablated at the stimulation point in block 312. If not (i.e., determination block 310=No), a new stimulation point may be generated based on ECG data collected during previous stimulation(s) in block 302.

In some embodiments, the activation map may be used to determine whether CRT is appropriate for a patient. For example, if the cardiac output of a patient is not predicted to achieve an acceptable level after optimally placing pacemaker(s) or pacing leads, it may be determined that CRT is not appropriate for the patient.

In various embodiments, a workstation that may be use that includes the processing unit 400, the display 330, and wired or wireless connections to other hardware such as the CT/MRI device 108, the 3D camera 109, the ECG recorder 106, and/or the real-time imaging device 328. The workstation may also include an interface for controlling a surgical device, such as a catheter implantation device or other robotic surgical device.

Figure 11A:
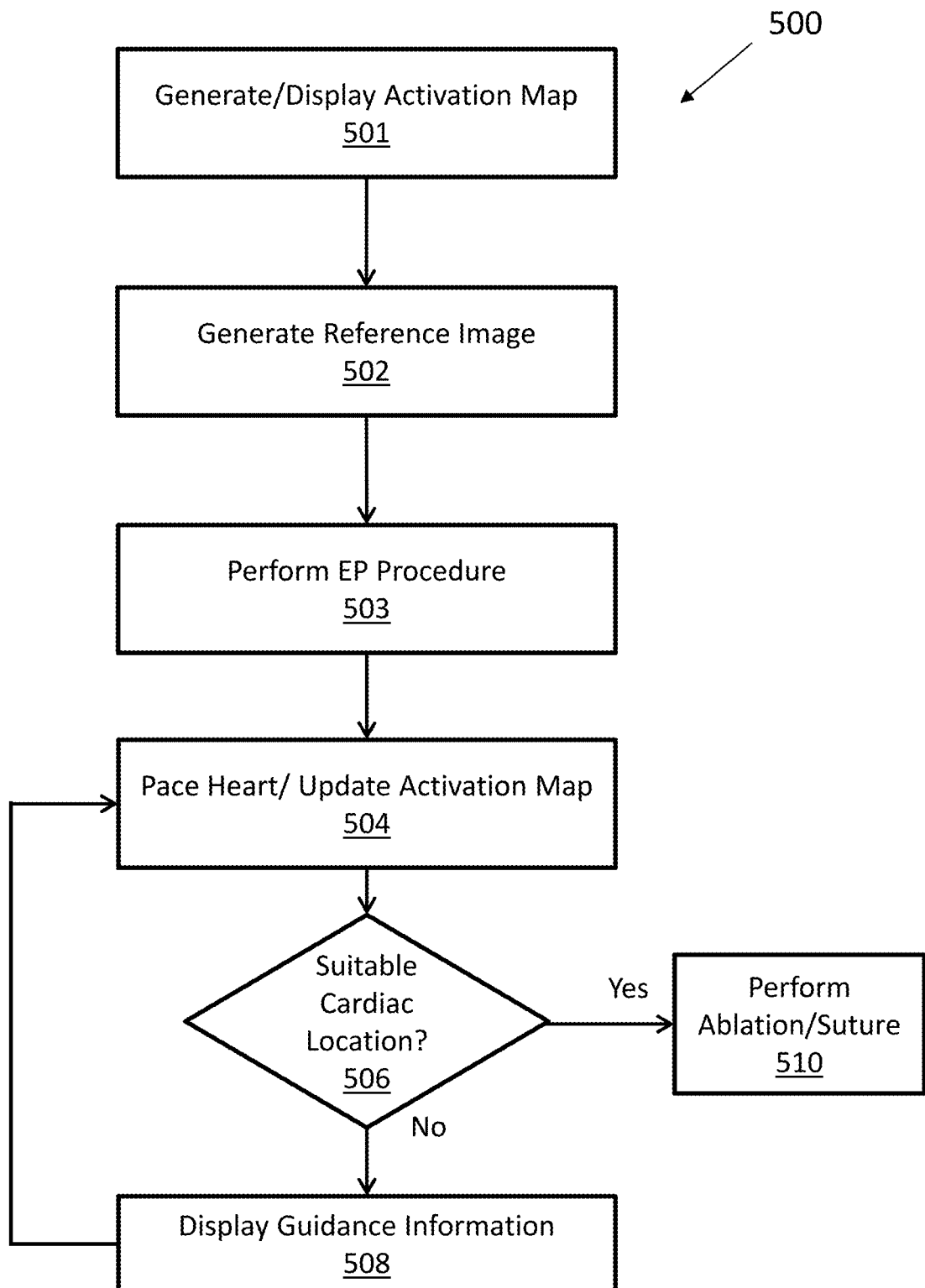
FIG. 11A is a flow diagram of a method of using the system of FIG. 9 according to various embodiments.
Figure 11B:
FIG. 11B illustrates an example of a reference cardiac image generated during the method of FIG. 11A.
Figure 11C:
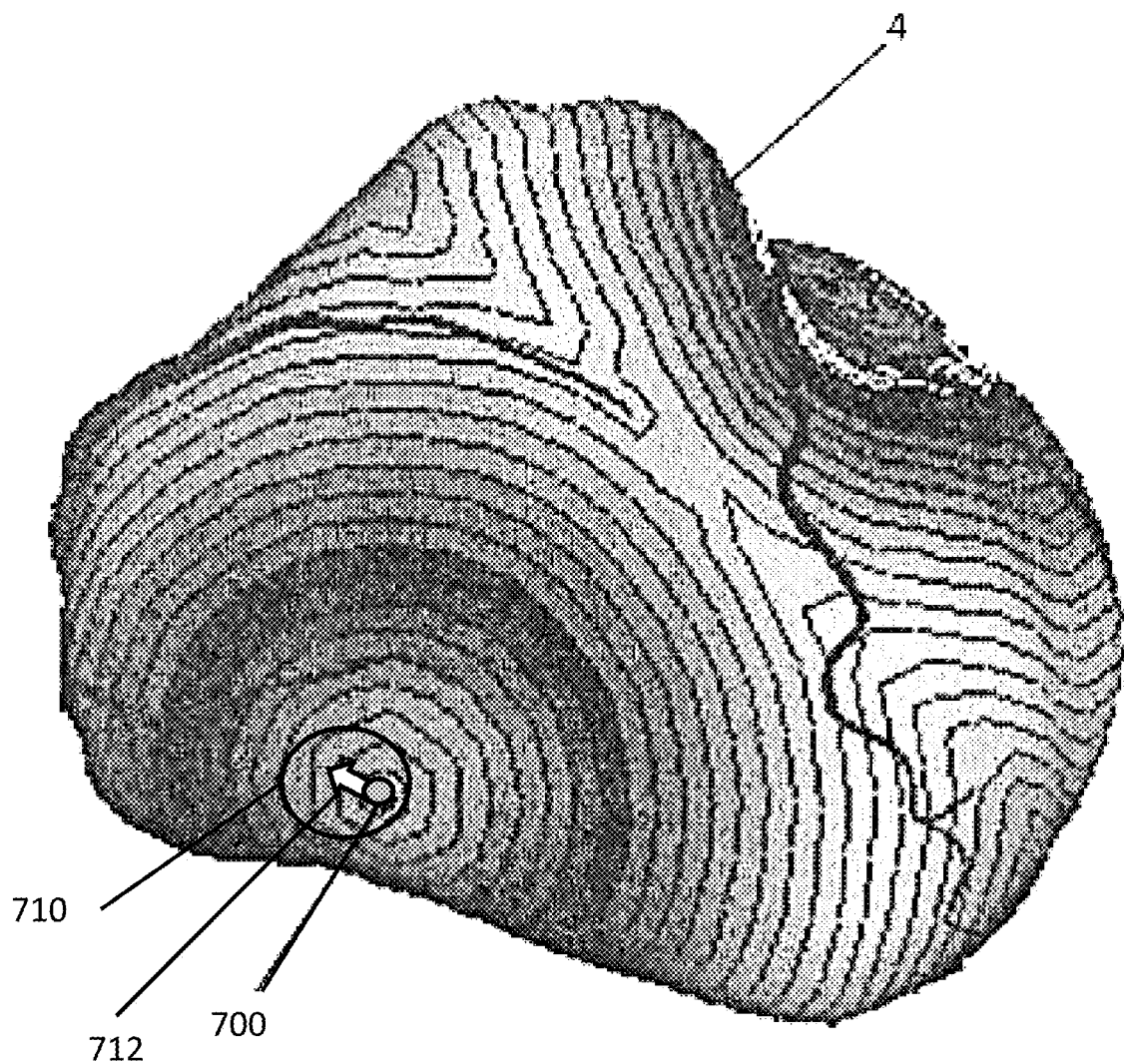
FIGS. 11C and 11D show activation maps that may be generated during the method of FIG. 11A.

FIG. 11A is a flow diagram illustrating a cardiac imaging method 500 using the system of FIG. 9 according to various embodiments. FIGS. 11B and 11C show activation maps that may be generated during the method of FIG. 11A.

Ablation is an effective treatment for PVC and/or VT. However, some patients may experience episodic VT and/or PVC, in which case the events or symptoms may not occur while a patient is tested at a hospital during a catheterization procedure or at electrophysiology facility during electrophysiology testing. To ensure sufficient ECG data is obtained for patients exhibiting episodic symptoms of VT and/or PVC, the ECG data may be recorded using a portable ECG recording device 106, such as a Holter-type device.

Referring to FIGS. 9 and 11A, the processing unit 400 may generate a PVC activation map, showing electrical activation during PVC in block 501. For example, the PVC activation map may identify an area of earliest activation during PVC. The PVC activation map may be based on ECG data collected during PVC, in addition to CT and/or MRI data from the patient as discussed above. In particular, the data may be provided to an activation map generator 320 of the processing unit 400. In some embodiments, ECG data from a single PVC beat may be sufficient to generate the PVC activation map. The PVC activation map may identify an area of the heart where earliest activation during the PVC heartbeat.

In some embodiments, the method may optionally include block 502. In block 502, the processor 400 may be used to generate a reference image showing internal structures of the heart. The activation map and the reference image may be displayed on the same display or on different displays, at the same time or at different times. In other words, blocks 501 and 502 may include providing the generated activation map and the reference image to the display 330.

The reference image may be based on a cardiac image, such as one of the 2D MRI or CT images used to generate the activation map. In addition to the internal cardiac structures shown in the cardiac image, the reference image may also include additional features. For example, to form the reference image, a cardiac image may be modified to show structures included in an area of earliest activation and/or virtual pacing location(s) included in the activation map.

In some embodiments, the processing unit 400 may be configured to select a cardiac image that most closely approximates an image being provided by the real-time imaging device 328, as discussed in block 503. In other embodiments, the reference image may be based on a manually selected cardiac image. Accordingly, the reference cardiac image could be referred to when positioning electrodes using the real-time imaging device 328.

FIG. 11B illustrates an example of a reference image for PVC/VT patients. Referring to FIG. 11B, the reference image may identify an area of earliest activation 340 (e.g., may identify cardiac structures in a 2D image that are included in the area of earliest activation. The reference image may also include a pacing location 342. The pacing location 342 may be a virtual pacing location generated by the stimulation point generator 324. In some embodiments, the pacing location 342 may be an actual pacing/catheter location. For example, when the heart is paced, the processing unit 400 may analyze the resulting ECG data to identify the corresponding pacing location 342, and thereby identify the current location of a pacing catheter, pacing electrode, etc.

In some embodiments, if the pacing location 342 does not provide a desired cardiac response, such as the simulation of PVC or a desired cardiac synchronicity, a guidance information generator 332 may provide guidance information, such as a vector 344 showing a direction in which the electrode should be moved.

In block 503, the method includes performing an electrophysiology (EP) procedure that includes inserting a catheter into the heart to analyze electrical activity and determine where an arrhythmia is located. In PVC patients, the goal of the EP procedure may be to pace the heart at a location that results in PVC that closely approximates the patient's symptomatic PVC. For example, the EP procedure may include pacing the heart using the catheter, at a location in the area of earliest activation. Additional electrodes may also be inserted to internally detect ECG data during the EP procedure. For example, pacing data may be recorded by recording ECG data during the pacing.

The EP procedure may also include mapping internal features of the patient's heart, such as features in and around the PVC area of earliest activation. In some embodiments, the EP procedure may include generating a 3D triangulated internal surface model, on a point-by-point basis, by contacting the different points of the heart with the catheter. Suitable systems for performing the EP procedure include the EnSite Precision mapping system and the Carto 3 mapping system. Such systems have the ability to track the 3D location of the catheter within the body and record an internal heart surface location every time contact between the catheter and heart tissue occurs. The collection of these 3D locations is synchronized with the heartbeat, so as to ensure that each point is collected when the heart is in the same state as the other recorded points (i.e. full volume as opposed to contracted). In addition to building a model, relative ECG activation times may be recorded and mapped onto the heart model.

Block 503 may also include generating a real-time image of the heart using the real-time imaging device 328, as described above. In some embodiments, block 502 may be performed after the real-time image is generated, such that the reference image may be based on a cardiac image that approximates the real-time image.

The EP procedure may also include positioning the catheter in contact with a location in the area of earliest activation. In block 504, the catheter may then be used to pace the heart via electrical stimulation. The goal of the pacing may be to pace the heart at a location that results in PVC that closely approximates the patient's symptomatic PVC. Additional electrodes may also be inserted to internally detect ECG data during the EP procedure. For example, pacing data may be recorded by recording ECG data during the pacing.

Although the EP procedure and the pacing are shown as separate blocks in FIG. 11A, the present disclosure is not limited thereto. For example, the EP procedure and the pacing may both occur during a single procedure.

In some embodiments, block 504 may include using the collected ECG data to generate an updated activation map to show the effect of the stimulation. In some embodiments, the ECG data may be used to identify the pacing location, which may be displayed on the activation map. Since the pacing electrode is disposed at the pacing location, the pacing location may represent the current location of the pacing electrode. Accordingly, pacing electrode locations may be displayed while navigating to a pacing location. As such, additional mapping applications may not be needed for determining the location of a pacing electrode, thereby substantially reducing costs of a pacing procedure.

In determination block 506, the pacing data may be analyzed to determine whether a pacing electrode is disposed in a suitable cardiac location for achieving a desired cardiac response. For example, the pacing data may be compared to the ECG data used to generate the activation map. In PVC, the pacing may be analyzed to determine whether the pacing data sufficiently matches the PVC ECG data recorded during presentation of the patient's PVC. In other words, the pacing data is analyzed to determine whether the catheter has identified a location that may be ablated to alleviate the patient's PVC and/or VT. In CRT patients, the pacing data may be analyzed to determine whether sufficient cardiac synchrony and/or activation have been achieved.

If it is determined that a desired cardiac response has been achieved (i.e., determination block 506=Yes), the catheter may be used to ablate the heart at the ablation location in PVC patients in block 510. In CRT patients, pacing electrodes and/or micro pacemakers may be sutured in position in block 510.

If it is determined that a desired cardiac response has not been achieved (i.e., determination block 506=No), the processing unit 400 may use the pacing data, PVC ECG data, and/or catheter location data to identify a direction the catheter should be moved in order to better simulate the patient's PVC in block 508. For example, the pacing data and catheter location data may be provided to a guidance information generator 332 of the processing unit 400. The guidance information generator 332 may include an algorithm configured to compare the pacing data and/or location data to the PVC ECG data, in order to determine a direction and/or a distance the catheter should be moved to properly simulate the patient's PVC. This information may be presented using icons and/or text. In CRT patients, the pacing data may be analyzed to determine whether one or more pacing electrodes should be moved to achieve a desired cardiac response.

The guidance information generator 332 may provide the guidance information to the activation map generator 320. The activation map generator 320 may update the activation map based on the guidance information provided by the guidance information generator 332, as discussed below with regards to FIGS. 11B and 11C. In other embodiments, the guidance information generator 332 may provide the guidance information to the image integrator 326 for integration with an image provided by the real-time imaging device 328. In other embodiments, the guidance information may be provided to the EP system and displayed on an EP map generated thereby.

After guidance information is displayed in block 508, the method returns to block 504 to again pace the heart. However, in some embodiments, the method may return to block 503 perform an EP procedure. Accordingly, in PVC/VT patients, a number of locations may be stimulated, until pacing results in PVC that accurately replicates the patient's PVC, and the corresponding ablation location is identified. In CRT patients, stimulation locations may be adjusted until a desired cardiac response is achieved. In addition, a physician may be provided with guidance information to assist in identifying stimulation points.

In some embodiments, block 503 may include using the mapping system of FIG. 9 to externally record ECG data during the pacing of the heart. Further, block 504 may also include using the mapping system to determine the pacing location within the heart, based on the recorded ECG data.

For example, the pacing location may be determined by identifying the area of earliest activation during the pacing of the heart. Further, block 508 may also include adding the pacing location to the PVC activation map. As such, the location of at least the pacing electrode of the catheter may be identified on the PVC activation map, since the pacing electrodes are disposed at the pacing location during pacing.

Referring to FIG. 11C, an updated activation map may include a first point 700 showing a pacing/stimulation location that corresponds to a most recent pacing location and/or catheter location. The updated activation map may also include an area of earliest activation 710, which may be a target area for ablation. In some embodiments, the activation map may include a vector 712 showing a direction and distance recommendation for moving the catheter to a new stimulation location in the area of earliest activation 710.

Figure 11D:
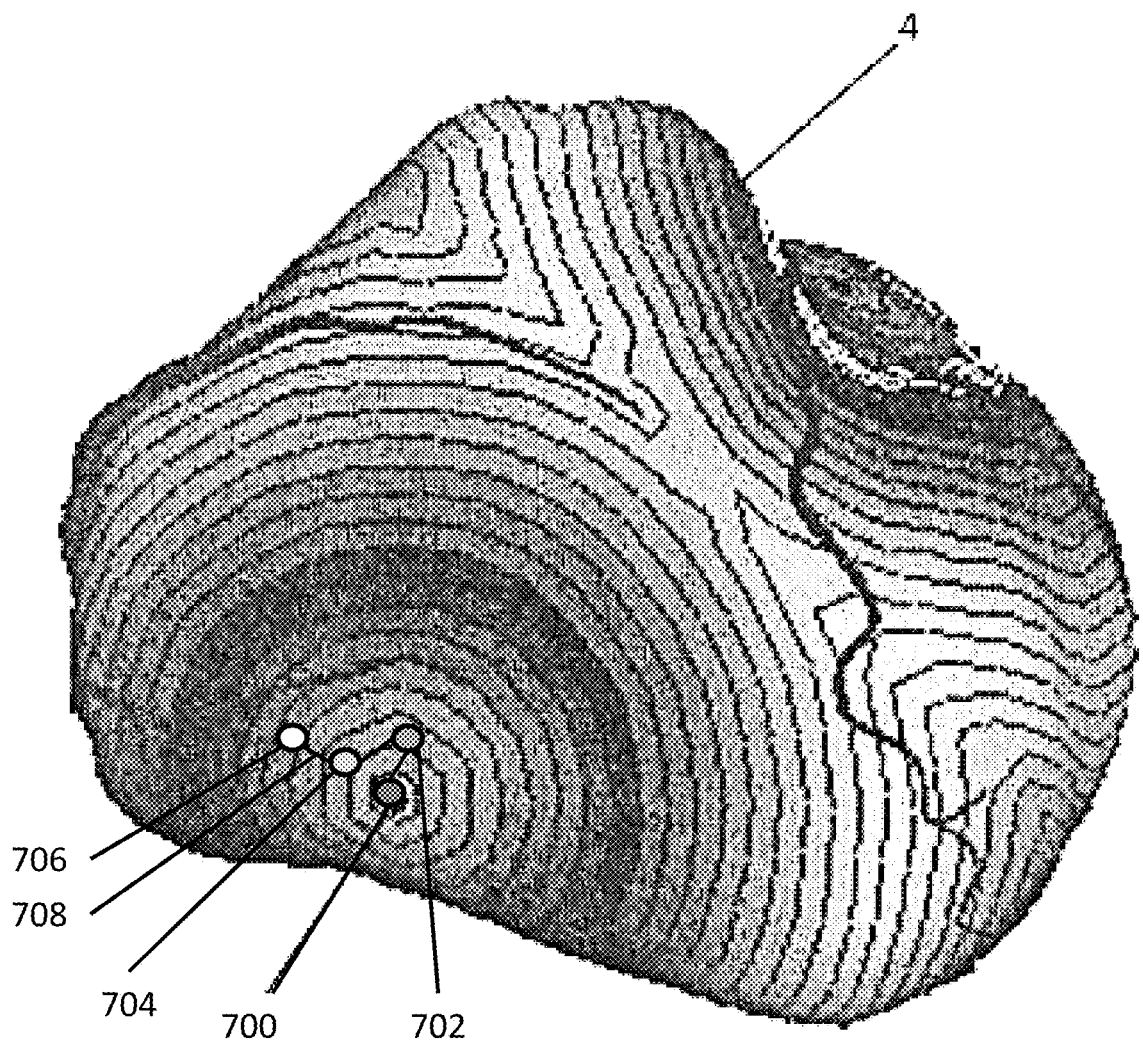

In some embodiments, as shown in FIG. 11D, the updated activation map may include one or more third points 704 showing previous pacing locations. For example, the updated activation map may include a first point 700 representing a first stimulation location, a second point 702 representing a second stimulation location, a third point 704 representing a third (e.g., current) stimulation location, and a fourth point 706 representing a suggested stimulation location. In some embodiments, the area of earliest activation 710 may be recalculated based on ECG data from each pacing.

The points 700-706 may be different colors, shades, and/or shapes to provide chronological information. For example, the points 700-706 may be shaded to represent an order in which the points were created, thereby identifying a path of the catheter. For example, the points 700-706 may be progressively lighter or darker. In some embodiments, the fourth point 706 may be lighter than the other points. Once pacing occurs at a location represented by the fourth point 706, the points 700-706 may each be darkened, or otherwise modified to indicate that the points represent previous pacing locations.

In other embodiments, points may be connected by lines 708 to represent a path of the catheter during the EP process. In some embodiments, the vector 712 of FIG. 11B may also be applied to the activation map of FIG. 11C, in addition to, or in place of, the fourth point 706.

Figure 12:
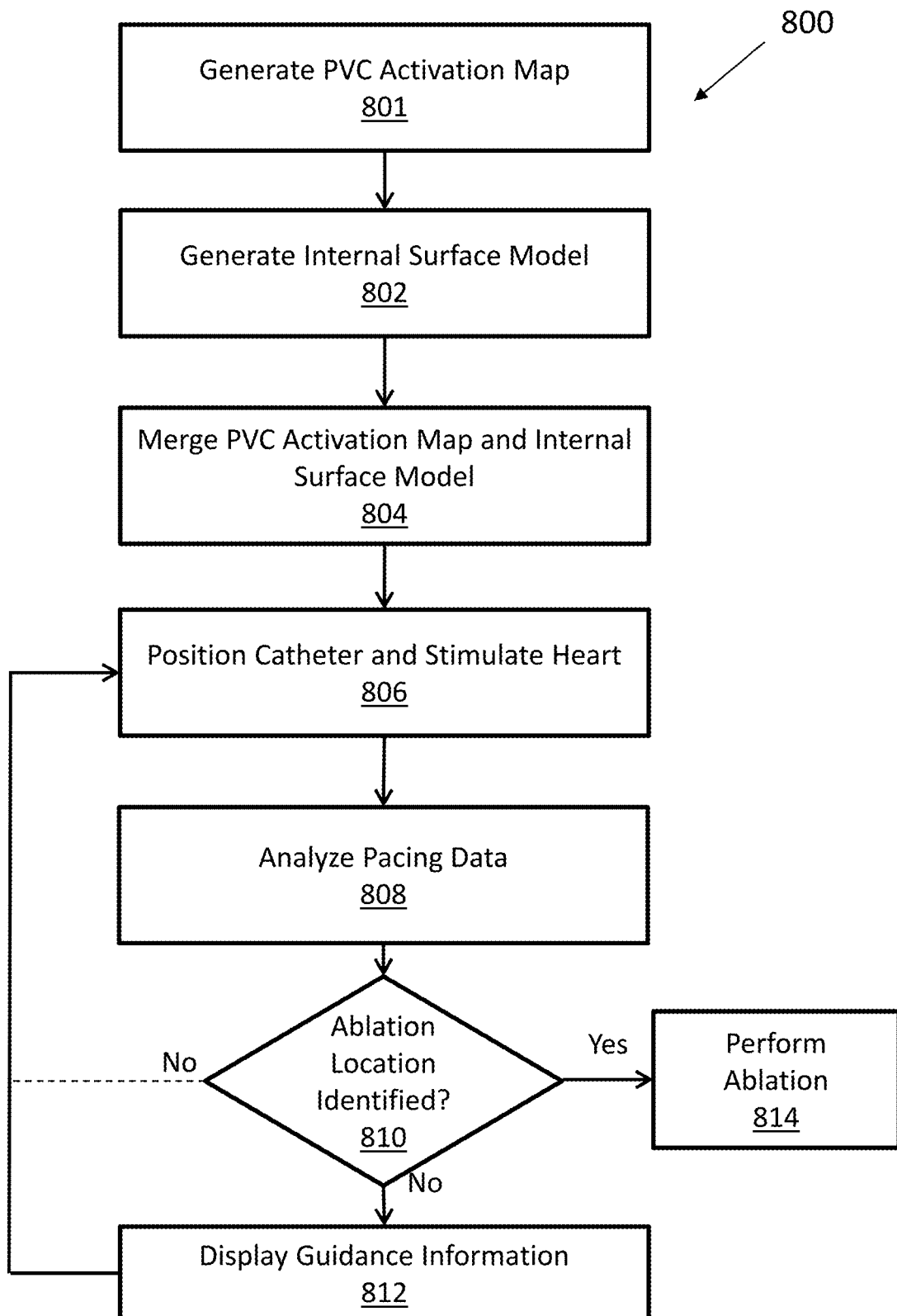
FIG. 12 is a flow diagram of a method of using the system of FIG. 9 according to various embodiments.

FIG. 12 is a block diagram illustrating an image integration method 800 according to various embodiments. The method 800 may be performed using the system of FIG. 9. Referring to FIGS. 9 and 12, in block 801, a PVC activation map of a patient's heart may be generated using the processor 400, as discussed above.

In block 802, a 3D internal surface model of the heart may be generated on a point-by-point basis through 3D triangulation. In particular, internal surface features of the patient's heart, such as ventricular surface features may be mapped on a point-by-point basis, by point contact between the internal surface of the heart and an EP catheter. Suitable systems for performing the EP procedure include the EnSite Precision mapping system and the Carto 3 mapping system. Such systems have the ability to track the 3D location of the catheter within the body and record a heart surface location every time contact between the catheter and heart tissue occurs. The collection of this point-by-point contact data is synchronized with heartbeat, so as to ensure that each point is collected when the heart is in the same state as the other recorded contact points (i.e., the volume of the heart is substantially the same). For example, the heart may be at full volume or full contraction, when the point contact is made.

In conventional EP systems, the internal surface model is merged with an acquired MRI or CT dataset to form a heart model. In particular, the merging may include adjusting the inner surface model data to more accurately represent the true geometry of the heart, as well as show additional cardiac features not mapped by during the EP procedure. This process involves a calculation of which point magnitudes within the CT or MR represent tissue versus blood. An adjustment can then be made to better represent the cardiac geometry.

The EP procedure may also involve recording relative ECG data (e.g., activation times) during the point-by-point contact. In some embodiments, this ECG data may be mapped onto the internal surface model. This may involve mapping normal ECG signals, since this allows for points to be collected quickly, as soon as cardiac/catheter contact occurs.

In order to determine an ablation point, a PVC activation map may be generated, since a PVC activation map includes an area of earliest activation during PVC. However, when generating a PVC activation map using a conventional EP system, the catheter must be in contact with the heart during PVC. Since PVC may only occur intermittently, using conventional methods to generate a PVC activation map may require a significantly longer amount of time, as compared to when non-symptomatic ECG data is utilized. This increases patient stress and the use of surgical resources.

As such, in block 804, the internal surface model generated in block 802 may be merged with the PVC activation map generated in block 801, to form a PVC activation surface model. In particular, the PVC activation data included in the PCV activation map may be applied to the internal surface model. Further, surface features included in the PVC activation map, which already includes MRI or CT data, may be merged with the triangulated point-by-point data included in the internal surface model. As such, the PVC internal surface model may be generated without performing the conventional process of merging of the triangulated point-by-point data and MRI or CT data, which further simplifies the process.

In block 806, the catheter may be positioned in the PVC earliest activation area shown on the EP PVC activation model, and the heart may be paced. Pacing ECG data may be recorded during the pacing.

In block 808, the pacing data may be analyzed to determine whether an ablation location has been identified. In particular, the pacing data may be analyzed to determine whether the pacing data sufficiently matches the ECG data recorded during onset of the patient's PVC. In other words, the pacing data is analyzed to determine whether the catheter has paced a location that may be ablated to alleviate the patient's PVC and/or VT.

In determination block 810, a determination is made whether an ablation location has been identified. If an ablation location has been identified (i.e., determination block 810=Yes), the catheter is used to ablate the heart at the identified ablation location in block 814.

If an ablation location is not identified (i.e., determination block 810=No), guidance information may be provided in block 812 as discussed above with regard to the method of FIG. 11A. The method may then proceed to block 806. However, in some embodiments, block 812 may be omitted and the method may proceed directly from determination block 810 to block 806 when an ablation location is not identified (i.e., determination block 810=No). The method 800 may then repeated until an ablation location is identified and ablated in block 814.

In some embodiments, the method may include displaying pacing locations on the PVC activation map. For example, the PVC activation surface model may be registered with the PVC activation map, and the pacing locations may be added to the PVC activation map. The pacing locations may also represent the location of the EP catheter during the pacing. In other embodiments, the processing unit 400 may analyze ECG data recorded during the pacing to determine the pacing and/or pacing catheter location and which may then be added to the PVC activation map.

In some embodiments, the method 800 may include generating and displaying a reference image with the PVC activation map and/or displaying guidance information, as discussed above with regard to FIGS. 11A-11D.

Some embodiments include hardware systems including a processing unit configured with software to receive patient-specific data, generate and display a 3D model of electrical activation of the heart in the form of a synchronicity map of the patient's heart based on ECG imaging data, and correlate or register the 3D model/map with the patient's body using recognizable markers on the body that serve as fiducial reference points (referred to herein as "fiducial markers"). An external imaging system, such as a 3D camera, may be used to obtain 3D image data of the patient's body (e.g., the torso or chest) with key anatomical reference points (e.g., clavicles, shoulders, ribs, etc. indicated by the markers applied to the patient by a clinician as part of the set up for a CRT procedure. The patient-specific 3D anatomical model may merge the image data with a 3D anatomical model of the patient's chest by registering the identified anatomical locations with corresponding anatomical locations in imaging obtained from CT or MRI scans.

Figure 13:
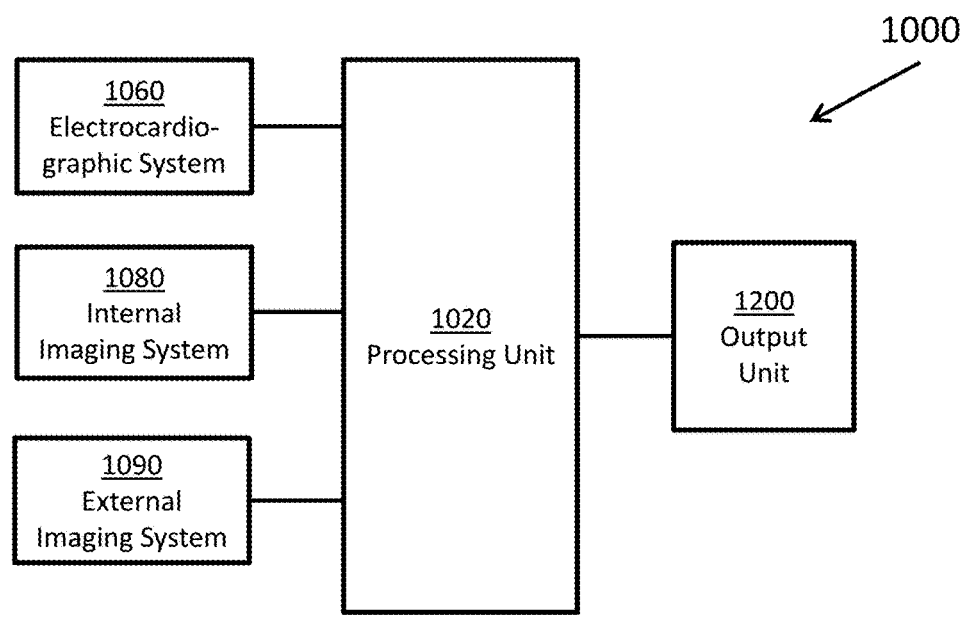
FIG. 13 is a system block diagram of a cardiac imaging system, according to various embodiments.

FIG. 13 is a system block diagram of a cardiac imaging system 1000, according to various embodiments. Referring to FIG. 13, the system 1000 includes a processing unit 102 which may be electrically connected to hardware modules, such as an electrocardiographic system 106, an internal imaging system 1080, an external imaging system 1090, and an output unit 1200.

The processing unit 1020 receives patient-specific data from the hardware modules. From the patient-specific anatomical data, the processing unit 1020 may generate a synchronicity map of the patient's heart, which may be output to the output unit 1200. The output unit 1200 may be configured to output the synchronicity map and/or alternative data to a user. The output unit may be a display unit, a printer, a messaging unit, or the like.

For example, the processing unit 1020 may receive electrocardiographic (ECG) imaging data from the electrocardiographic system 1060, such as a 12 lead ECG device. The ECG data may be used by the processing unit 1020 for determining the 3D model 4 of electrical activation of the heart. In particular, ECG signals may be combined with a patient-specific 3D anatomical model of the heart, lungs, and/or torso, in order to compute the positions of the cardiac isochrones.

The patient-specific 3D anatomical model may be obtained from the internal imaging system 1080, such as an MRI device or CT device. Alternatively or additionally, a 3D anatomical model showing closest conformity to the patient may be selected, and optionally modified, from a database including a plurality of 3D anatomical models. The selected, and optionally modified, 3D anatomical model may serve as the patient-specific 3D anatomical model.

Further, the processing unit 1020 may receive patient image data from the external imaging system 1090. For example, the external imaging system 1090 may be 3D camera, and the processing unit 1020 may receive 3D image data of the surface a patient's chest, as shown in FIG. 14A or 14B.

Figure 14A:
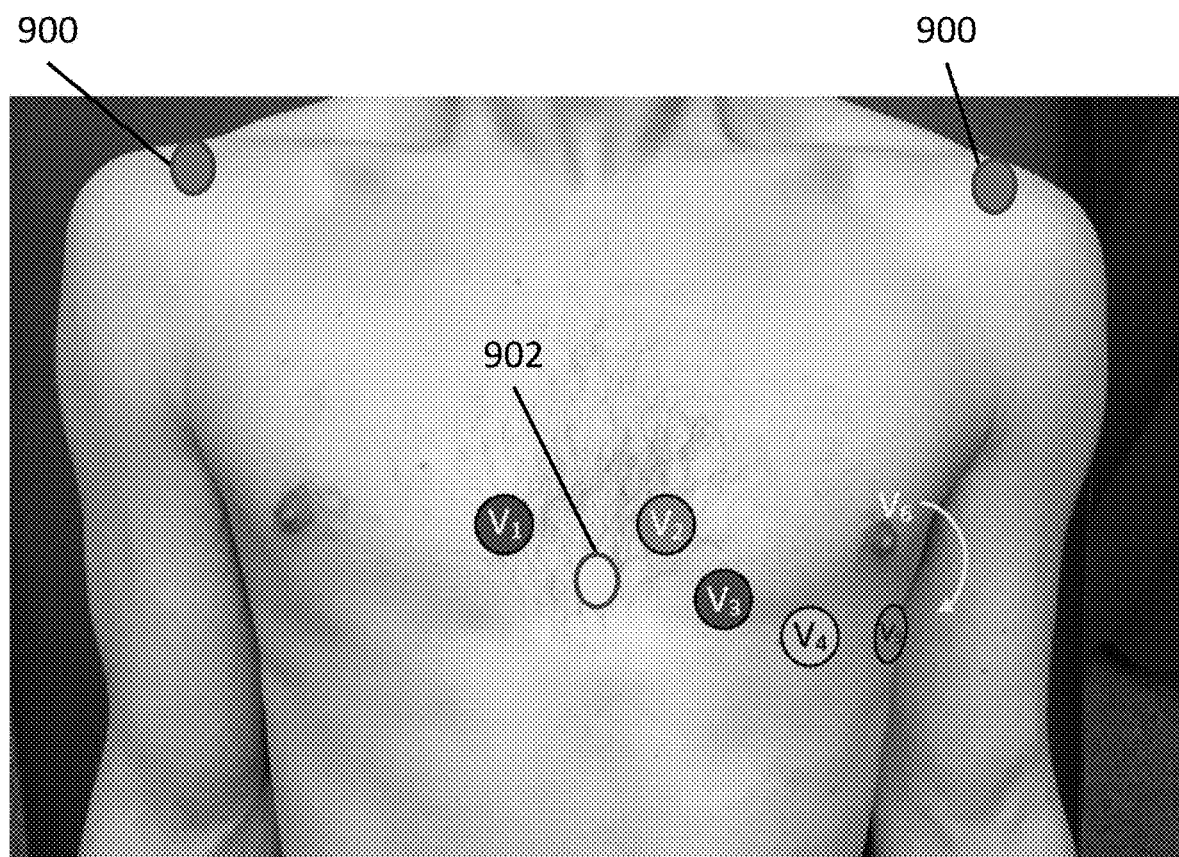
FIGS. 14A and 14B are 3D images of electrical leads and fiducial markers on a patient's torso according to various embodiments.
Figure 14B:
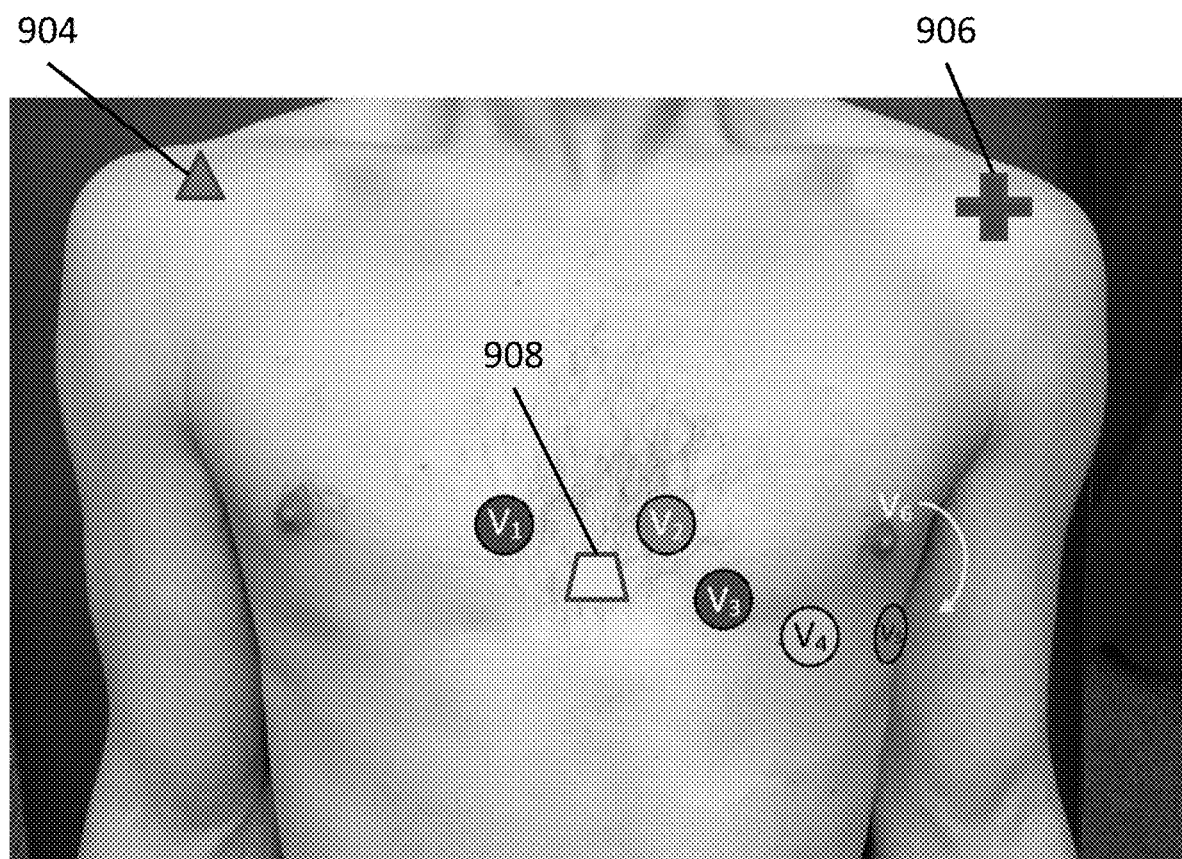

Referring to FIG. 14A, the 3D image data may include positions of ECG leads relative to the anatomy of the patient, such as the V1-6 precordial electrodes shown in FIG. 14A. Knowledge of the location of the ECG electrodes relative to the heart, and in particular the V1-6 precordial electrodes, may be especially important for accurately computing the onset location of PVC.

In some embodiments, the offsets of the electrodes from their assumed ideal locations, and in particular offsets of the V1-6 electrodes, may be determined based on a comparison of detected ECG signals of a normal heart beat to ideal ECG normal heart beat signals. For example, the offsets may be determined based on how a detected ECG signal will be affected by variations in the position of electrodes with respect to ideal electrode positions. In particular, the recorded ECG data may be used to determine a stimulation onset location for a normal beat. Since the normal onset location in the SA node is known, the determined offset location may be compared to this known onset location, and the offset of the electrodes may be deduced based on the variation therebetween. As such, it may be possible to determine electrode offsets without generating the 3D map.

The processing unit 1020 may be configured to align and/or merge the 3D image data generated by the external imaging system 1090 and the anatomical torso and/or heart model generated by the internal imaging system 1080, and the locations of the electrodes in the torso model may be adjusted to coincide with the electrode locations in the 3D image data. However, if the external imaging system 1090 is not properly aligned with the torso, it may be difficult to properly the 3D image data and the anatomical model.

In order to facilitate the alignment of the 3D image data and the anatomical torso model, the system 100 may include fiducial markers placed on (e.g., adhered to) a patient's torso prior and captured in the 3D image data generated by the external imaging system 109. The fiducial markers may be placed on the patient by a clinician in set anatomical locations that are identified in the torso model in order to facilitate alignment of the 3D image of the patient with the anatomical torso model. In some embodiments, the fiducial markers may be stickers having an adhesive backing configured to adhere to the skin, with a shape, color and/or surface material (e.g., reflective or retroreflective material) that enables automatic identification and location of the markers by a processor processing the 3D image data.

For example, first fiducial markers 900 may be placed on the patient's shoulders at set anatomical locations, such as at the distal end of each clavicle. A second fiducial marker 902 may be placed at a set anatomical location between the first fiducial markers 902, such as at a set position on the patient's sternum.

The processing unit 1020 may be configured to identify the fiducial markers 900, 902, and anatomical locations corresponding thereto, based on one or more identifying characteristics thereof included in the 3D image data collected by an external imaging device. In some embodiments, the processing unit 1020 may be configured to identify anatomical locations corresponding to the fiducial markers 900, 902, based on the color, shape, and/or reflectivity of the corresponding anatomical markers included in the image data.

In some embodiments, the fiducial markers 900, 902 may be configured to reflect specific wavelengths of light. For example, the first fiducial markers 900 may have a first color and the second fiducial marker 902 may have a second color. In some embodiments, each marker 900, 902 may have a different color.

In some embodiments the fiducial markers 900, 902 may include a reflective material, which may be in the form of a reflective coating. In some embodiments, the reflective material may be configured to reflect one or more specific wavelengths, or wavelength ranges, of light. For example, in some embodiments the fiducial markers 900, 902 may be formed of materials configured to reflect visible light, infrared light, ultraviolet light, or a combination thereof. In some embodiments, the external imaging system 1090 may include a light source, and the reflective material may be configured to reflect all or some of the light emitted from the light source. For example, the fiducial markers 900, 902 may be configured to selectively reflect particular wavelengths or wavelength ranges of the emitted light. The processing unit 1020 may be configured to identify the fiducial markers 900, 902 based on the light reflected thereby.

In some embodiments, the fiducial markers 300, 302 may include a retroflective material. In particular, the retroflective material may be configured to reflect incident light, or a portion thereof, at an angle substantially equal to the angle of incidence of the incident light (i.e., directly back towards the source of the incident light). Retroflective materials are well known as used in safety vests and on traffic signs, for example. In such embodiments, the processing unit 102 may be configured to detect such light as a luminosity peak in the image data received from the external imaging system.

In some embodiments, the fiducial markers may have one or more different shapes. For example, as shown in FIG. 14B, the system 1000 may include triangular fiducial marker 904, a cross-shaped fiducial marker 906, and/or a trapezoidal fiducial marker 908. The processing unit 1020 may be configured to identify anatomical locations corresponding to the fiducial markers, based on the shapes thereof.

However, various embodiments are not limited to any particular fiducial marker identifying characteristics, so long as the fiducial markers include a characteristic identifiable by the processing unit 1020 and detectable by the external imaging system 1090. Further, while three fiducial markers are shown in FIGS. 14A and 14B, any suitable number of fiducial markers may be used.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable medium or non-transitory processor-readable medium. The steps of a method or algorithm disclosed herein may be embodied in a processor-executable software module and/or processor-executable instructions, which may reside on a non-transitory computer-readable or non-transitory processor-readable storage medium. Non-transitory server-readable, computer-readable or processor-readable storage media may be any storage media that may be accessed by a computer or a processor. By way of example but not limitation, such non-transitory server-readable, computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory server-readable, computer-readable and processor-readable media. Additionally, the operations of a method or algorithm may reside as one or any combination or set of codes and/or instructions on a non-transitory server-readable, processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A cardiac mapping method comprising:
generating an activation map of a heart using electrocardiogram (ECG) data of the heart and a three-dimensional (3D) heart model;
performing an electrophysiology (EP) procedure to determine a first pacing location;
pacing the heart at the first pacing location using an EP catheter;
determining whether the pacing at the first pacing location generates a desired cardiac response;
displaying guidance information related to a second pacing location on one or both of the activation map and an internal surface map of the 3D heart model when the first pacing location does not generate the desired cardiac response;
moving the EP catheter to the second pacing location, based on the guidance information; and
pacing the heart at the second pacing location.

2. The method of claim 1, wherein displaying guidance information comprises displaying a vector pointing from the first pacing location towards the second pacing location.

3. The method of claim 1, wherein displaying guidance information comprises:
displaying a first point representing the first pacing location; and
displaying a vector pointing from the first point towards the second pacing location.

4. The method of claim 1, wherein displaying guidance information comprises:
displaying a first point representing the first pacing location; and
displaying a second point representing the second pacing location.

5. The method of claim 1, further comprising recording first ECG data during the pacing of the first pacing location, wherein:
the activation map is generated using premature ventricular contraction (PVC) ECG data; and
determining whether the pacing at the first pacing location generates a desired cardiac response comprises determining whether the first pacing location is an ablation location that may be ablated to prevent the PVC by comparing the first ECG data to the PVC ECG data.

6. The method of claim 5, wherein the method further comprises:
recording second ECG data during pacing of the second pacing location;
determining whether the second pacing location is an ablation location that may be ablated to prevent the PVC by comparing the second ECG data to the PVC ECG data;
displaying guidance information related to a third pacing location on one or both of the activation map and the internal surface map when the second pacing location is not an ablation location; and
moving the EP catheter to the third pacing location using the guidance information.

7. The method of claim 6, wherein displaying guidance information comprises:
displaying a first point representing the first pacing location;
displaying a second point representing the second pacing location; and
displaying a third point representing the third pacing location.

8. The method of claim 7, wherein displaying guidance information comprises displaying the first, second, and third points in different shades, based on a path of the catheter.

9. The method of claim 7, wherein displaying guidance information comprises displaying lines connecting the first, second, and third points based on a point-by-point path of the catheter.

10. The method of claim 5, wherein:
the activation map comprises an area of earliest activation; and
displaying guidance information comprises displaying an updated area of earliest activation on the activation map based on the comparison of the PVC ECG data and the first ECG data.

11. The method of claim 5, further comprising:
recording second ECG data during pacing of the first pacing location; and
determining whether the second pacing location is a suitable ablation location based on a comparison of the second ECG data and the PVC ECG data.

12. The method of claim 11, further comprising ablating the heart at the second pacing location in response to determining that the second pacing location is an ablation location.

13. The method of claim 1, wherein the 3D heart model is generated using magnetic resonance (MRI) images or computed tomography (CT) images of the heart.

14. The method of claim 1, further comprising:
recording first ECG data during the pacing of the first pacing location; and
identifying the second pacing location by analyzing the first ECG data.

15. The method of claim 1, wherein:
the internal surface model of the heart is a point-by-point triangulated surface model; and
displaying guidance information comprises displaying the guidance information on the triangulated surface model.

16. The method of claim 1, wherein determining whether the pacing at the first pacing location generates a desired cardiac response comprises determining whether the pacing at the first pacing location generates a desired amount of cardiac resynchronization.

17. A cardiac mapping method comprising:
generating a PVC activation map of a heart, using premature ventricular contraction (PVC) electrocardiogram (ECG) data and a three-dimensional (3D) heart model generated using two-dimensional (2D) images of the heart;
recording first ECG data while pacing the heart at a first pacing location disposed in the area of earliest activation included in the PVC activation map, using a catheter;
determining whether the first pacing location is an ablation location by comparing the PVC ECG data and the first ECG data;
displaying guidance information related to a second pacing location when the first pacing location is not to be an ablation location;
moving the catheter to the second pacing location based on the guidance information; and
pacing the heart at the second pacing location using the catheter.

18. The method of claim 17, further comprising generating an internal surface map of the heart using an electrophysiology (EP) procedure, wherein pacing the heart at the second pacing location using the catheter is performed during the EP procedure.

19. A cardiac mapping method comprising:
- generating an activation map of a heart using electrocardiogram (ECG) data of the heart and a three-dimensional (3D) heart model;
- performing an electrophysiology (EP) procedure to pace the heart at a first pacing location using an EP catheter;
- determining whether the pacing at the first pacing location generates at least a set amount of cardiac synchronization;
- displaying the guidance information related to a second pacing location on one or both of the activation map and an internal surface map of the 3D heart model when the first pacing location generates less than the set amount of synchronization;
- moving the pacing catheter to the second pacing location based on the guidance information; and
- pacing the heart at the second pacing location.

20. The method of claim 19, wherein displaying guidance information comprises displaying a vector pointing from the first pacing location towards the second pacing location.

21. The method of claim 19, wherein displaying guidance information comprises:
- displaying a first point representing the first pacing location; and
- displaying a vector pointing from the first point towards the second pacing location.

22. The method of claim 19, wherein displaying guidance information comprises:
- displaying a first point representing the first pacing location; and
- displaying a second point representing the second pacing location.

* * * * *